United States Patent [19]

Hadlaczky

[11] Patent Number: 5,712,134
[45] Date of Patent: Jan. 27, 1998

[54] METHOD OF PRODUCING A CELL CARRYING AN EXCESS OF MAMMALIAN CENTROMERES

[75] Inventor: Gyula Hadlaczky, Szamos, Hungary

[73] Assignee: The Biological Research Center of the Hungarian Academy of Sciences, Hungary

[21] Appl. No.: 375,271

[22] Filed: Jan. 19, 1995

Related U.S. Application Data

[63] Continuation of Ser. No. 80,097, Jun. 23, 1993, abandoned, which is a continuation of Ser. No. 892,487, Jun. 3, 1992, abandoned, which is a continuation of Ser. No. 521,073, May 9, 1990, abandoned.

[51] Int. Cl.$^6$ ............................................. C12N 15/09
[52] U.S. Cl. ................................. 435/172.2; 435/172.3; 935/42
[58] Field of Search ............................ 435/91, 172.3, 435/172.2; 935/42

[56] References Cited

U.S. PATENT DOCUMENTS

| | | | |
|---|---|---|---|
| 4,518,584 | 5/1985 | Mark et al. | 424/85 |
| 4,608,339 | 8/1986 | Yoakum et al. | 435/172.2 |
| 4,684,611 | 8/1987 | Schilperoort et al. | 435/172.3 |
| 4,686,186 | 8/1987 | Sugden | 435/243 |
| 4,784,737 | 11/1988 | Ray et al. | 204/180.1 |
| 4,806,476 | 2/1989 | Coons et al. | 435/172.2 |
| 4,873,191 | 10/1989 | Wagner et al. | 435/172.3 |
| 4,935,350 | 6/1990 | Patel et al. | 435/69.4 |
| 4,970,162 | 11/1990 | Aksamit | 435/240.26 |
| 4,997,764 | 3/1991 | Dalla Favera | 435/240.27 |
| 5,019,034 | 5/1991 | Weaver et al. | 604/20 |
| 5,144,019 | 9/1992 | Rossi et al. | 536/27 |
| 5,149,796 | 9/1992 | Rossi et al. | 536/27 |
| 5,162,215 | 11/1992 | Bosselman et al. | 435/172.3 |
| 5,215,914 | 6/1993 | Lo et al. | 435/253.1 |
| 5,223,263 | 6/1993 | Hostetler et al. | 424/445 |
| 5,240,840 | 8/1993 | Feinberg et al. | 435/172.3 |
| 5,240,846 | 8/1993 | Collins et al. | 435/240.1 |
| 5,260,191 | 11/1993 | Yang | 435/6 |
| 5,266,600 | 11/1993 | Tenmyo et al. | 514/691 |
| 5,272,262 | 12/1993 | Rossi et al. | 536/23.2 |
| 5,288,625 | 2/1994 | Hadlaczky | 435/172.2 |
| 5,292,658 | 3/1994 | Cormier et al. | 435/252.33 |
| 5,298,429 | 3/1994 | Evans et al. | 436/501 |
| 5,324,655 | 6/1994 | Kriegler et al. | 435/240.2 |
| 5,354,674 | 10/1994 | Hodgson | 435/172.3 |
| 5,358,866 | 10/1994 | Mullen et al. | 435/240.2 |
| 5,364,761 | 11/1994 | Ariga | 435/6 |
| 5,396,767 | 3/1995 | Suzuki | 60/298 |
| 5,409,810 | 4/1995 | Larder et al. | 435/5 |
| 5,413,914 | 5/1995 | Franzusoff | 435/23 |
| 5,418,155 | 5/1995 | Cormier et al. | 435/189 |
| 5,424,409 | 6/1995 | Ely et al. | 536/23.71 |
| 5,434,086 | 7/1995 | Collins et al. | 436/125 |
| 5,436,392 | 7/1995 | Thomas et al. | 800/205 |
| 5,449,604 | 9/1995 | Schellenberg et al. | 435/6 |
| 5,453,357 | 9/1995 | Hogan | 435/7.21 |
| 5,461,032 | 10/1995 | Krapcho et al. | 514/12 |
| 5,468,615 | 11/1995 | Chio et al. | 435/7.2 |
| 5,468,634 | 11/1995 | Liu | 435/240.2 |
| 5,470,708 | 11/1995 | Yang et al. | 435/6 |
| 5,470,730 | 11/1995 | Greenberg et al. | 435/172.3 |
| 5,482,928 | 1/1996 | De Bolle et al. | 514/12 |
| 5,489,520 | 2/1996 | Adams et al. | 435/172.3 |
| 5,491,075 | 2/1996 | Desnick et al. | 435/69.7 |
| 5,496,731 | 3/1996 | Xu et al. | 435/320.1 |
| 5,501,662 | 3/1996 | Hofmann | 604/20 |
| 5,501,967 | 3/1996 | Offringa et al. | 435/172.3 |
| 5,503,999 | 4/1996 | Jilka et al. | 435/172.3 |

FOREIGN PATENT DOCUMENTS

| | | | |
|---|---|---|---|
| 0240373 | 10/1987 | European Pat. Off. | |
| A-240373 | 10/1987 | European Pat. Off. | |
| 0254315 | 1/1988 | European Pat. Off. | |
| 0350052 | 1/1990 | European Pat. Off. | A01K 67/02 |
| 0375406 | 6/1990 | European Pat. Off. | |
| 0473253 | 3/1992 | European Pat. Off. | C12N 15/85 |
| 9100358 | 1/1991 | WIPO | C12N 15/87 |
| 9419456 | 9/1994 | WIPO | C12N 5/00 |
| 9500178 | 1/1995 | WIPO | A61K 48/00 |
| 9507643 | 3/1995 | WIPO | A47C 7/20 |
| 9514769 | 6/1995 | WIPO | C12N 5/00 |
| 9520044 | 7/1995 | WIPO | |
| 9532297 | 11/1995 | WIPO | |

OTHER PUBLICATIONS

Brown et al., Mammalian artificial chromosomes, *Current Opinion: Genetics and Devt.* 6: 281–288 (1996).

Chisari et al., A transgenic mouse model of the chronic hepatitis B surface antigen carrier state, *Science* 230: 1157–1160 (1985).

Hadlaczky et al., Centromere proteins I. Mitosis specific centromere antigen recognized by anti-centromere autoantibodies, *Chromosoma* 97:272–288 (1989).

Henikoff et al., Position-effect variegation after 60 years, *Trends in Genetics* 6: 422–426 (1990).

Kappel et al., Regulating gene expression in transgenic animals, *Current Biology*, pp. 548–553, (1992).

Klotman et al. Transgenic models of HIV-1, *Current Sci Ltd.* 9:313–324, (1995).

Larsson et al. Reduced β2–microglobulin mRNA levels in transgenic mice expressing a designed hammerhead ribozyme, *Nucleic Acids Research* 22:2242–2248, (1994).

Strojek et al. The use of transgenic animal techniques for livestock improvement, *Genetic Engineering: Principles and Methods* 10:221–246, (1988).

DIALOG Abstract 007268905, citing: EP 0240 373 A1 (1987).

(List continued on next page.)

*Primary Examiner*—Keith D. Hendricks
*Attorney, Agent, or Firm*—Stephanie L. Seidman; Brown, Martin, Haller and McClain

[57] ABSTRACT

DNA fragments and methods for obtaining them are disclosed which when put into mammalian cells together with a dominant marker gene are able to generate functional centromeres. The sequences can be used to form probes for these centromeres. Cell lines containing the functional centromeres are also provided. Methods are taught for isolating mammalian centromeric DNA as well as for producing cell lines carrying an excess of mammalian centromeres linked to a dominant selectable marker gene.

11 Claims, 18 Drawing Sheets

OTHER PUBLICATIONS

DIALOG Abstract 007389041, citing EP 0254 315 (1988).
Baker et al., Suppression of human colorectal carcinoma cell growth by wild–type p53, *Science* 249:912–915 (1990).
Biggin et al., Buffer gradient gels and $^{35}$S label as an aid to rapid DNA sequence determination, *Proc. Natl. Acad. Sci. USA*, 80:3963–3965 (1983).
Blattner et al., Charon phages: Safer derivatives of bacteriophage lambda for DNA cloning, *Science* 196:16 (1977).
Bostock and Christie, Analysis of the frequency of sister chromatid exchange in different regions of chromosomes of the Kangaroo rat (*Dipodomys ordii*), *Chromosoma* 56: 275–287 (1976).
Bostock and Clark, Satellite DNA in large marker chromosomes of methotrexate–resistant mouse cells, *Cell* 19: 709–715 (1980).
Brewer and Fangman, The localization of replication origins on ARS plasmids in *S. cerevisiae*, *Cell* 51: 463–471 (1987).
Brisson and Hohn, [27] Plant virus vectors: Cauliflower mosaic vectors, *Methods for Plant Molecular Biology*, Weissbach et al., eds. Adacemic Press, N.Y., Section VIII, pp. 437–446 (1988).
Brown, Mammalian artificial chromosomes, *Curr. Opin. Genes Dev.* 2:479–486 (1992).
Bullock and Botchan, Molecular events in the excision of SV40 DNA from the chromosomes of cultured mammalian cells. In: *Gene Amplification.*, Schimke RT, ed. Cold Spring Harbor, NY: Cold Spring Harbor Laboratory Press, pp. 215–224 (1982).
Burhans et al., Identification of an origin of bidirectional DNA replication in mammalian chromosomes, *Cell* 62: 955–965 (1990).
Burhans and Huberman, DNA replication origins in animal cells—a questionof context? *Science* 263: 639–640 (1994).
Carrano and Wolff, Distribution of sister chromatid exchanges in the euchromatin and heterochromatin of the Indian muntjac, *Chromosoma* 53: 361–369 (1975).
Chalfie et al., Green fluorescent protein as a marker for gene expression, *Science* 263:802–804 (1994).
Chang et al., Ribozyme–mediated site–specific cleavage of the HIV–1 genome, *Clin. Biotech.* 2:23–31 (1990).
Chen et al., High–efficiency transformation of mammalian cells by plasmid DNA, *Mol. Cell. Biol.* 7:2745–2752 (1987).
Chen et al., Genetic mechanismof tumor suppression by the human p53 gene, *Science* 250:1576 (1990).
Chikashige et al., Composite motifs and repeat symmetry in *S. pombe* centromeres: Direct analysis by integration of NotI restriction sites, *Cell* 57:739–751 (1989).
Church, Replication of chromatin in mouse mammary epithelial cells grown in vitro, *Genetics* 52: 843–849 1985.
Colbère–Garapin et al., A new dominant hybrid selective marker for higher eukaryotic cells, *J. Mol. Biol.* 150:1–14 (1981).
Collins and Newlon, Chromosomal DNA replication initiates at the same origins in meiosis and mitosis, *Mol Cell Biol* 14: 3524–3534. (1994).
Cooper and Tyler–Smith, The putative centromere–forming sequence of λCM8 is a single copy sequence and is not a component of most human centromeres, *Hum. Mol. Gen.* 1(9):753–754 (1992).
Couto et al., Inhibition of intracellular histoplasma capsulatum replication by murine macrophages that produce human defensin, *Infect. Immun.* 62:2375–2378 (1994).

Cram et al., Polyamine buffer for bivariate human flow cytogenetic analysis and sorting, *Methods in Cell Biology* 33:377–382 (1990).
Current state of the art, *Chromos Molecular Systems—News Release* (May 29, 1996) (available at http://www.chromos.com/contents.html).
Cutler, Electroporation: Being developed to transform crops, *Ag Biotechnology News* 7:3 (Sep./Oct. 1990).
Davidson et al., Improved techniques for the induction of mammalian cell hybridisation by polyethylene glycol, *Somatic Cell. Genet.* 2:165–176 (1976).
Dean et al. Multiple mutations in highly conserved residues are found in mildly affected cystic fibrosis patients, *Cell* 61:863–870 (1990).
DePamphilis, Eukaryotic DNA replication: Anatomy of an origin, *Ann. Rev. Biochem.* 62:29–63 (1993).
Dunckley et al., Retroviral–mediated transfer of a dystrophin minigene into mdx mouse myoblasts in vitro, *FEBS Lett.* 296:128–34 (1992).
Erlich et al., Recent advances in the polymerase chain reaction, *Science* 252:1643–1651 (1991).
Fangman and Brewer, A question of time: replication origins of eukaryotic chromosomes, *Cell* 71: 363–366 (1992).
Farr et al., Generation of a human X–derived minichromosome using telomere–associated chromosome fragmentation, *EMBO J.* 14:5444–5454 (1995).
Farrel et al., p53 is frequently mutated in Burkitt's lymphoma cell lines, *EMBO J.* 10:2879–2887 (1991).
Fátyol et al., Cloning and molecular characterization of a novel chromosome specific centromere sequence of Chinese hamster, *Nucl. Acids Res.* 22:3728–3736 (1994).
Fechheimer et al., Transfection of mammalian cells with plasmid DNa by scrape loading and sonication loading, *Proc. Natl. Acad. Sci. USA* 84:8463–8467 (1987).
Ford and Fried, Large inverted duplications are associated with gene amplification, *Cell* 45:425–430, (1986).
Fournier, A general high–efficiency procedure for production of microcell hybrids, *Proc. Natl. Acad. Sci. USA* 78:6349–6353 (1981).
French et al., Construction of a retroviral vector incorporating mouse VL30 retrotransposon–derived, transcriptional regulatory sequences, *Anal. Biochem* 228:354–355 (1995).
Frohman and Martin, Cut, paste, and save: new Approaches to altering specific genes in mice, *Cell* 56:145–147 (1989).
Fromm et al., Expression of genes transfered into monocot and dicot plant cells by electroporation, *Proc. Natl. Acad. Sci. USA* 82:5824–5828 (1985).
Gillespie et al., Tissue–specific expression of human Cd4 in transgenic mice, *Mol. Cell. Biol.* 13:2952–2958 (1993).
Gluzman, SV40–transformed simian cells support the replication of early SV40 mutatnts, *Cell* 23:175–182 (1981).
Goodfellow et al., Techniques for mammalian genome transfer, in *Genome Analysis a Practical Approach*, K.E. Davies, ed., IRL Press, Oxford, Washington DC. pp. 1–17 (1989).
Graham and van der Eb, A new technique for the assay of infectivity of human adenovirus 5 DNA , *Virology* 52:456–457 (1973).
Grierson et al., *Plant Molecular Biology*, 2d Ed., Blackie, London, Ch. 7–9 (1988).
Gritz et al., Plasmid–encoded hygromycin B resistance: The sequence of hygromycin B phosphotransferase gene and its expression in *Escherichia coli* and *Saccharomyces cerevisiae*, *Gene* 25:179–188 (1983).
Guide to Techniques in Mouse Development, *Methods in Enzymology* 25:803–932 (1993).

Gunning et al., A human β–actin expression vector system directs high–level accumulation of antisense transcripts, *Proc. Natl. Acad. Sci. USA* 84:4831–4835 (1987).

Haase et al., Transcription inhibits the replication of autonomously replication plasmids in human cell, *Mol. Cell. Biol.* 14:2516–2524 (1994).

Hadlaczky et al., Centromere formation in mouse cells cotransformed with human DNA and a dominant marker gene, *Proc. Natl. Acad. Sci. USA* 88:8106–8110 (1991).

Hadlaczky et al., Protein depleted chromosomes, *Chromosoma* 81:537–555 (1981).

Hadlaczky et al., Direct evidence for the non–random localization of mammalian chromosomes in the interphase nucleus, *Exp. Cell Res.* 167:1–15 (1986).

Hadlaczky and Szalay, Mammalian artificial chromosomes: Potential vectors for gene therapy, Abstract from International Symposium on *Gene Therapy of Cancer, AIDS and Genetic Disorders*, Trieste (Italy) (Apr. 10–13, 1996) (available at http://www.chromos.com/contents.html).

Hadlaczky and Szalay, Mammalian artificial chromosomes: Introduction of novel genes into mammalian artificial chromosomes, Abstract from International Symposium on *Gene Therapy of Cancer, AIDS and Genetic Disorders*, Trieste (Italy) (Apr. 10–13, 1996) (available at http://www.chromos.com/contents.html).

Hadlaczky et al., Structure of isolated protein–depleted chromosomes of plants. *Chromosoma* 86:643–659 (1982).

Hadlaczky, Structure of metaphase chromosomes of plants, *Internatl. Rev. Cytol.* 94:57–76 (1985).

Hall et al., Expression and regulation of *Escherichia coli* lacZ gene fusions in mammalian cells, *J. Mol. Appl. Gen.* 2:101–109 (1983).

Handeli et al., Mapping replication units in animal cells, *Cell* 57 909–920 (1989).

Hanna et al., Specific expresion of the human DC4 gene in mature $CD4^+$ $CD8^-$ and immature $CD4^+$ $CD8^+$ T cells and in macrophages of transgenic mice, *Mol. Cell. Biol.* 14:1084–1094 (1994).

Harper et al., Localization of single copy DNA sequences on G–banded human chromosomes by in situ hybridization, *Chromosoma* 83:431–439 (1981).

Hassan et al., Replication and transcription sites are colocalized in human cells. *J. Cell. Sci.* 107:425–434 (1994).

Hilwig and Gropp, Decondensation of constitutive heterochromatin in L cell chromosomes by a benzimidazole compound ("33258 Hoechst"), *Exp Cell Res* 81: 474–477 (1973).

Hogan et al., *Manipulating the Mouse Embryo: A Laboratory Manual*, Cold Spring Harbor Laboratory Press, Cold Spring Harbor, NY, pp. 253–289, see, especially pp. 255–264 and Appendix 3 (1994).

Hollo et al., Evidence for a megareplicon covering megabases of centrome segments, *Chromosome Research* 4:1–14 (1996) (available at http://www.chromos.com/contents.html).

Holmquist and Comings, Sister chromatid exchange and chromosome organisation based on a bromodeoxyuridine Giemsa–C–banding technique (TC–banding), *Chromosoma* 52:245–259 (1975).

Hsu and Markvong, Chromosomes and DNA in Mus; Terminal DNA synthetic sequences in three species, *Chromosoma* 51:311–322 (1975).

Huberman and Riggs, On the mechanism of DNA replication in mammalian chromosomes, *J Mol Biol* 32:327–341 (1968).

Huberman et al., The in vivo replication origin of the yeast 2 μm plasmid. *Cell* 51:473–481 (1987).

Huxley, Mammalian artificial chromosomes: a new tool for gene therapy, *Gene Therapy*, 1:7–12 (1994).

Hyde et al., Correction of the ion transport defect in cystic fibrosis transgenic mice by gene therapy, *Nature* 362: 250–255 (1993).

Hyrien et al., The multicopy appearance of large inverted duplication and the sequence at the inversion joint suggest a new model for gene amplification, *EMBO J* 7:407–417 (1988).

Ish–Horowitz et al., Rapid and efficient cosmid cloning. *Nucleic Acids Res.* 9:2989–2998 (1981).

Jacob et al., On the regulation of DNA replication in bacteria, *Cold Spring Harb Symp Quant Biol* 28:329–348 (1963).

Joy and Gopinathan, Expression of microinjected foreign DNA in the silkworm, *Bombex mori*, *Current Science* 66:145–150 (1991).

Keown et al., Methods for introducing DNA into mammalian cells, *Meth. Enzymol.* 185:527–537 (1990).

Kerem et al., Identification of the cystic fibrosis gene: genetic analysis, *Science* 245:1073–1080 (1989).

Kereso et al., De novo chromosome formations by large–scale amplification of the centromeric region of mouse chromosomes, *Chromosome Research* 4:1–14 4:226–239 (1996) (available at http:www.chrommos.com/contents.html).

Kitsberg et al., Replication structure of the human b–globin gene domain, *Nature* 366:588–590 (1993).

Korenberg et al., Human genome organization: Alu, LINES, and the molecular structure of metaphase chromosome bands, *Cell* 53:391–400 (1988).

Kornberg and Baker, *DNA Replication*. 2nd. ed., New York: W.H. Freeman and Co, p. 474 (1992).

Lambert et al., Functional complementation of ataxia–telangiectasia group D (AT–D) cells by microcell–mediated chromosome transfer and mapping of the AT–D locus to the region 11q22–23, *Proc. Natl. Acad. Sci. USA* 88:5907–59 (1991).

Lawrence et al. Sensitve, high–resolution chromatin and chromosome mapping in situ: Presence and orientation of two closely integrated copies of EBV in a lmphoma line, *Cell* 52:51–61 (1988).

Leder et al., EK2 derivatives of bacteriophage lambda useful in the cloning of DNA from higher organisms: The λgtWES system, *Science* 196:75–177 (1977).

Liu et al., The pro region of human neutrophil defensin contains a motif that is essential for normal subcellular sorting, *Blood* 85:1095–1103 (1995).

Locardi et al., Persistent infection of normal mice with human immunodeficiency virus, *J. Virol.* 66:1649–1654 (1992).

Looney et al., The dihydrofolate reductase amplicons in different methotrexate–resistant Chinese hamster cell lines share at least a 273–kilobase core sequence, but the amplicons in some cell lines are much larger and remarkably uniform in structure, *Mol. Cell Biol.* 8:5268–5279 (1988).

Lorenz et al., Isolation and expression of a cDNA encoding *Renilla reniformis* luciferase, *Proc. Natl. Acad. Sci. USA* 88:4438–4442 (1991).

Lorenz et al., Expresion of the *Renilla reniformis* licuferase gene in mammalian cells, *J. Biolum. Chemilum.* 11:31–37 (1996).

Ma et al., Sister chromatid fusion initiates amplification of the dihydrofilate reductase gene in Chinese hamster cells, *Genes Develop.* 7:605–620 (1993).

Ma et al., Organisation and genesis of dihydrofolate reductase amplicons in the genome of a methotrexate–resistant Chinese hamster ovary cell line, *Mol. Cell Biol.* 8:2316–2327 (1988).

Madan et al., Fluorescence anlaysis of late DNA replication in mouse metaphase chromosomes using BUdR and 33258 Hoechst, *Exp. Cell Res.* 99:438–444 (1976).

Maniatis et al., The isolation of structural genes from libraries of eucaryotic DNA, *Cell* 15:687–701 (1978).

Mansour et al., Disruption of the proto–oncogene int–2 in mouse embryo–derived stem cells: a general strategy for targeting mutations to non–selectable genes, *Nature* 336:348–352 (1988).

Matthews et al., Purification and properties of *Renilla reniformis* luciferase, *Biochemistry* 16:85–91 (1977).

Maxwell et al., Regulated expression of a diphtheria toxin A–chain gene transfected into human cells: possible strategy for inducing cancer cell suicide, *Cancer Res.* 46:4660–4664 (1986).

McGill et al., λCM8, a human sequence with putative centromeric function, does not map to the centromere but is present in one or two copies at 9qter, *Hum. Mol. Gen.* 1(9):749–751 (no date available).

Meinkoth and Wahl, Hybridization of nucleic acids immobilized on solid supports, *Anal. Biochem.* 138:267–284 (1984).

Meyne et al., Distribution of non–telomeric sites of the (TTAGGG)$_n$ telomeric sequence in vertebrate chromosomes, *Chromosoma* 99:3–10, (1990).

Miller, in *Experiments in Molecular Genetics*, Cold Spring Harbor Press, pp. 352–355 (1972).

Miller, Is the centromeric heterochromatin of *Mus musculus* late replication? *Chromosoma* 55:165–170 (1976).

Miller and Rosman, Improved retroviral vectors for gene transfer and expression, *Biotechniques* 7:980–990 (1989).

Mitani et al., Delivering therapeutic genes—matching approach and application, *Trends Biotech.* 11:162–166 (1993).

Morgan and French Anderson, Human gene therapy, *Annu. Rev. Biochem.* 62:191–217 (1993).

Morgenstern et al., Advanced mammalian gene transfer: High titre retroviral vectors with multiple drug selection markers and a complementary helper–free packaging cell line, *Nucleic Acids Res.* 18:3587–3596 (1990).

Mulligan, The basic science of gene therapy, *Science* 260:926–932 (1993).

Nabel et al., Site–specific gene expression in vivo by direct gene transfer into the arterial wall, *Science* 249:1285–1288 (1990).

Nikolaev et al., Microinjection of recombinant DNA into early embryos of the mulberry silkworm *Bombyx mori*, *Mol. Biol.* (Moscow) 23:1177–87 (1989).

O'Keefe et al., Dynamic organization of DNA replication in mammalian cell nuclei: Spatially and temporally defined replication of chromosome–specific a–satellite DNA sequences, *J. Cell Biol.* 116:1095–1110 (1992).

Osborne et al., A mutation in the second nucleotide binding fold of the cystic fibrosis gene, *Am. J. Hum. Genetics* 48:608–612 (1991).

Paszowski and Saul, [28] Direct gene transfer to plants, *Methods for Plant Molecular Biology*, Weissbach et al., eds., Academic Press, N.Y., Section VIII, pp. 447–463 (1988).

Perry and Wolff, A new Giemsa method for the differential staining of sister chromatids, *Nature* 251:156–158 (1974).

Pinkel et al., Cytogenetic analysis using quantitative, high-sensitivity, fluorescence hybridization, *Proc. Natl. Acad. Sci. USA*, 83:2934–2938 (1986).

Prasher et al., Primary structure of the *Aequorea victoria* green–fluorescent protein, *Gene* 111:229–233 (1992).

Praznovszky et al., De novo chromosome formation in rodent cells, *Proc. Natl. Acad. Sci. USA* 88:11042–11046 (1991).

Priest, Cytogenetics. In *Medical Technology Series*. R.M. French, M. Eichmam, B. Fiorella, and H.F. Weisberg, eds. (Lea and Febiger, Philadelphia) pp. 189–190 (1969).

Quaster et al., Cell population kinetics in the intestinal epithelium of the mouse, *Exp. Cell Res.* 17:420–438 (1959).

Report and recommendations of the panel to assess the NIH investment in research on gene therappy, Orkin and Motulsky, co–chairs (Dec. 7, 1995) (available at http://www.nih-.gov/news/panelrep.html).

Richia and Lo, Introduction of human DNA into mouse eggs by injection of dissected chromosome fragments, *Science* 245:175–177 (1989).

Riordan et al., Identification of the cystic fibrosis gene: cloning and characterization of complementary DNA, *Science* 245:1066–1072 (1989).

Rogers et al., [26] Gene transfer in plants: Production of transformed plants using Ti plasmid vectors, *Methods for Plant Molecular Biology*, Weissbach et al., eds., Academic Press, N.Y., Section VIII, pp. 423–436 (1988).

Rommens et al., Identification of the cystic fibrosis gene: chromosome walking and jumping, *Science* 245:1059–1065 (1989).

Rosenfeld et al., In vivo transfer of the human cystic fibrosis transmembrane conductance regulator gene to the airway epithelium, *Cell* 68:143–155 (1992).

Sambrook et al., *Molecular Cloning: A Laboratory Manual*, vol. 1. 2d Ed., Cold Spring Harbor Laboratory Press, Section 2.18 (1989).

Sanes et al., Use of a recombinant retrovirus to study post–implantation cell lineage in mouse embryos, *EMBO J.* 5(12):3133–3142 (1986).

Sanger et al., Cloning in single–stranded bacteriophage as an aid to rapid DNA sequencing, *J. Mol. Biol.* 143:161–178 (1980).

Saxon et al., Selective transfer of individual human chromosomes to recipient cells, *Mol. Cell. Biol.* 1:140–146 (1985).

Schedl et al., A method for the generation of YAC transgenic mice by pronuclear microinjection, *Nuc. Acids Res.* 21:4783–4787 (1993).

Scientists report a major step in ralizing the commercial potential of engineered artificial chromosomes in significant life sciences sectors, including gene therapy, *Chromos Molecular Systems—News Release* (May 29, 1996) (available at http://www.chromos.com/contents.html).

Selig et al., Regulation of mouse satellite DNA replication time, *EMBO J.* 7:419–426 (1988).

Smith et al., Distinctive chromosomal structures are formed very early in the amplification of CAD genes in Syrian hamster cells, *Cell* 63:1219–1227 (1990).

Sugden et al., A vector that replicates as a plasmid and can be efficiently selected in B–lymphoblast transformed by Epstein–Barr virus, *Mol. Cell. Biol.* 5:410–413 (1985).

Sumner, Scanning electron microscopy of mammalian chromosomes from prophase to telophase. *Chromosoma* 100:410–418 (1991).

Sumner, A simple technique for demonstrating centromeric heterochromatin, *Cell Res.* 75:304–306 (1972).

Szybalsky et al. Genetic studies with human cell lines, *Natl. Cancer Inst. Monogr.* 7:75–89 (1982).

Tamura et al., Microinjection of DNA into early embryo of *Bombyx mori*, *Bio Ind.* 8:26–31 (1991) (Chemical Abstracts # 114(21)200502z).

Toledo et al., Co–amplified markers alternate in megabase long chromosomal inverted repeats and cluster independently in interphase nuclei at early steps of mammalian gene amplification, *EMBO J.* 11:2665–2673 (1992).

Tonghua et al., Effects of antisense epidermal growth factor and its receptor retroviral expression vectors on cell growth of human pancreatic carcinoma cell line, *Chin. Med. J.* (Beijing, Engl. Ed.) 108:653–659 (1995).

Transfection of DNA into eukaryotic cells, *Current Protocols in Molecular Biology*, vol. 1, Wiley Inter–Science, Supplement 14, Unit 9.1.1–9.1.9 (1990).

Uchimiya et al., Transgenic plants, *J. Biotechnol.* 12: 1–20 (1989).

Vig and Richards, Formation of primary constriction and heterochromatin in mouse does not require minor satellite DNA, *Exp. Cell Res.* 201:292–298 (1992).

Wang and Fedoroff, Banding of human chromosomes treated with trypsin, *Nature* 235:52–54 (1972).

Weinberg, Tumor suppressor genes, *Science* 254:1138–1146 (1991).

White et al., A frame–shift mutation in the cystic fibrosis gene, *Nature* 344:665–667 (1990).

Why are MACs in vogue, *Chromos Molecular Systems—News Release* (May 29, 1996) (available at http://www.chromos.com/contents.html).

Wigler et a., DNA–mediated transfer of the adenine phosphoribosyltransferase locus into mammalian cells, *Proc. Natl. Acad. Sci. USA* 76:1373–1376 (1979).

Willard and Waye, Hierarchical order in chromosome specific human alpha satellite DNA, *Trends Genet.* 3:192–198 (1987).

Williams and Blattner, Construction and characterization of the hybrid bacteriophage lambda charon vectors for DNA cloning, *J. Virol.* 29:555–575 (1979).

Wong et al., Sequence organisation and cytological localization of the minor satellite of mouse, *Nucl. Acids Res.* 16:11645–11661 (1988).

Yamada et al., Multiple chromosomes carrying tumor suppressor activity for a uterine endometrial carcinoma cell line identified by microcell–mediated chromosome transfer, *Oncogene* 5:1141–1147 (1990).

Yates et al., Stable replication of plasmids derived from Epstein–Barr virus in various mammalian cells, *Nature* 313:812–815 (1985).

Yates et al., A cis–acting element from the Epstein–Barr viral genome that permits stable replication of recombinant plasmids in latently infected cells, *Proc. Natl. Acad. Sci. USA* 81:3806–3810 (1984).

Yeung et al., Human CD4–major histocompatibility complex class II (Dqw6) transgenic mice in an endogenous CD4/CD8–deficient background: reconstitution of phenotype and humano–restricted function, *J. Exp. Med.* 180:1911–1920 (1994).

Yurov, Identification and characterization of two distinct polymorphic α–satellite DNA sequences from centromeric regions of the chromosomes 13 and 21 (A2299), *Cytogenet. Cell Genet.* 51:1114 (1989).

Yurov, Collection of α–satellite DNA probes: Highly polymorphic markers for centromeric regions of all human chromosomes (A2298), *Cytogenet. Cell Genet.* 51:1114 (1989).

Brazolot et al., Efficient transfection of chicken cells by lipofection and introduction of transfected blastoderm cells into the embryo, *Mol. Repro. Dev.* 30:304–312 (1993).

Dieken et al., Efficient modification of human chromosomal alleles using recombination–proficient chicken/human microcell hybrids, *Nature Genet.* 12:174–182 (1996).

Etches et al., Chimeric chickens and their use in manipulation of the chicken genome, *Poultry Sci.* 72:882–889 (1993).

Frasier et al., Efficient incorporation of transfected blastodermal cells into chimeric chicken embryos, *Int. J. Dev. Biol.* 37:381–385 (1993).

Green et al., Chromosomal region of the cystic fibrosis gene in yeast artificial chromosomes: A model for human genome mapping, *Science* 250:94–98 (1990).

Jabs et al., Characterization of a cloned DNA sequence that is present at centromeres of all human autosomes and the X chromosome and shows polymorphic variation, *Proc. Natl. Acad.* 81:4884–4888, (1984).

Le Bolc'h et al., Cationic phosphonolipids as non viral vectors for DNA transfection, *Tetrahedron Lett.* 36:6681–6684 (1995).

Love et al., Transgenic birds by microinjection, *Bio/Technology* 12:60–63 (1994).

McLean, Improved Techniques for immortalizing animal cells, *TIBTECH* 11, 232–238 (1993).

Petitte et al. Production of somatic and germline chimeras in the chicken by transfer of early blastodermal cells, *Development* 108:185–189 (no date available).

Roth, Artifizielle chromosomen, *Natur Wissenschaften* 74:78–85, (1987).

Sang, Transgenic chickens—methods and potential applications, *TIBTECH* 12,415–420 (1994).

Smith et al., Amplification of large artificial chromosomes, *Proc. Natl. Acad. Sci. USA*, 87:8242–8246, (1990).

von Bodman et al., Expression of multiple eukaryotic cells from a single promoter in *Nicotina*, *Bio/Technology* 13: 587–591 (1995).

Waring et al., Nucleotide sequence repitition: A rapidly reassociating fraction of mouse DNA, *Science* 154:791–794 (1966).

Zang et al., Production of recombinant proteins in Chines hamster ovary cells using a protein–free cell culture medium, *Bio/Technology* 13: 389–392 (1995).

Bower, D.J. "Constructing a fully defined human Minichromosome: . . . " (Conference abstract) Source: Eur Cong. Biotechnol. (vol. 3 571) 1987.

Carine et al, "Chinese Hamster Cells with a Minichromosome Containing the Centromere Region of Human Chromosome 1", *Som. Cell & Mol. Gen.*, vol. 12, #5, 1986, pp. 479–491.

Solus et al., "Characterization of Single–Copy Probe from Vicinity of Centromere of Human Chromosome 1", *Som. Cell & Mol. Gen.*, vol. 14, No. 4, 1988, pp. 381–391.

Burke, et al., "Cloning of Large Segments of Exogenous DNA into Yeast by Means of Artificial Chromosome Vectors," Science, vol. 236, pp. 806–812 (no date available).

Murray et al., "Construction of Artificial Chromosomes in Yeast," Nature, vol. 305, pp. 189–193, Sep. 15, 1993.

Clarke et al., "The Structure and Function of Yeast Centromeres," Ann. Rev. Genet. 1985, 19:29–56.

Blackburn et al., "The Molecular Structure of Centromeres and Telomeres" Ann. Rev. Biochem., 1984, 53:163–94.

Hadlaczky, et al., "Centromere proteins: I. Mitosis specific centromere antigen recognized by anti–centromere autoantibodies", *Chromosoma*, 97(4):282–288, 1989.

FIG. 1A

```
         10         20         30         40         50         60         70         80         90        100
GAATTCATGC CAAGTGCAAG TCTGGGGGTC ACCTTGACTG GAGACCCTCC TCCCGCCACG TTCTTTGAAC TTCCCTCCAT CCGGTCCAAG TCTCTTCCAA
        110        120        130        140        150        160        170        180        190        200
TGCCATCCTC AGCCCTGCAG CAGCCCTCAC TCCCGATGCC TTCCCACCTC CTCACCACTC TGCCCCACCC TGGCCAGGCC ATCACCTCCA GGGCCCAACT
        210        220        230        240        250        260        270        280        290        300
TGGAGCCCCC AGGACCCTCC CGTGCCCTGC CTGATGTCCC GCCTGTCCCC ACAGAGCCTC ACTGGTCAC CACCCAGTCC TGGCCCTTGC TTACTGTGGC
        310        320        330        340        350        360        370        380        390        400
TGCACCCCGA GGTGTCCTAG GGTCTAGCAG GTGGCTGCCC AGACATGGAG GTAGAGGAAG GAGTGGGTGG GGATGGGCTT GTCCTGCCCA GGCCTCCCTG
        410        420        430        440        450        460        470        480        490        500
CCTGTCCTGC TGGCCACAGC CTTGGCTTGC CCAGGAGAAC CCATGGGCCA CACATCCCAC TGCCAATCCC ACACGTCCTT TCTGGGAAC ACCGTGGGGA
        510        520        530        540        550        560        570        580        590        600
AAGCTGTGGC ACCAGCTCCT TCCTTTTGCA ACTCTGATGA ATCTCACCCA GCCCACTCTC CACATCCCAC CACATCCCCA TCATAGGCCT CCCCCATCCC
        610        620        630        640        650        660        670        680        690        700
CTGGACACAC AGAGACACAC CTGGATTCAG GTCAGGCCTC GCCCACTCTC GGCTATATTT CTCCCCAAGC CGTGTGTCCT CAGCTGTAGA ATCAGGACCA
        710        720        730        740        750        760        770        780        790        800
TAAGGAAGTT CCCTCATAGG GTTCTTGTGA GGACGGCACG ATTTACGTAG GGGATGCTCA CTCCCCAAGC CACCGTGCCT GGCAGCTGGG ACGCACTCCA CCCGCGGCAG
        810        820        830        840        850        860        870        880        890        900
CCGGTCCCA TGCTTCTTCA CAGCCACACT GCACTTCTTA GACAGGAACA CTCCATACGA TGTCCCCTC CTGCACTGGA TGGCCCAAAA
        910        920        930        940        950        960        970        980        990       1000
ATCTGAAATA AGAGGAGGAG TGCGTGTGAA GCTCCCAGTG GAGGGTTTGG CACCTGTCCA CACCTGTCCC AAGGGCAAGT CACGGCTCTG AGATTCAGTG
       1010       1020       1030       1040       1050       1060       1070       1080       1090       1100
TCTCCTTCTG CAAGTAGGGC CAATAGTGGT TCCTCCCTCC CAGGGCTGAA GTGAGGATGA GATGGGATAA TCCACCCCCG TCCCACACC CTGCAGGTCA
       1110       1120       1130       1140       1150       1160       1170       1180       1190       1200
TCATCATTGC TAGCAGTTGT GTGGTGGGAGC AGGTGCTCTT GAGGGAGCGA CACCTCCAGG TGCTCCCCTG CCCTGCTGGC CCCTCTGCAG GAGGTGACAC
```

```
     1210       1220       1230       1240       1250       1260       1270       1280       1290       1300
CCAGGCCCCT TTCCCCTGGG GCAGCCAGCT CAGCCCCTCT CTCTCCCACA GGTGCCGCTG CAGTTCCTTT GGCAGTAAGT AACAGGCGCT GGGGAGGGTG
     1310       1320       1330       1340       1350       1360       1370       1380       1390       1400
GCCAGGGCCC CCACTGCACG CGCCTCTTTG CATGTCCTGG AAAAAGCAGG AGAGAAAAAA GGGGCTTCAG TGTCCCCTCT GGGACTTGGG CCATTCACTC
     1410       1420       1430       1440       1450       1460       1470       1480       1490       1500
CCTCCTCTAA TTACACCCCT ACTGCTTCTC CACCTCTCTC CCCTCCACCT CCCCCCCTCC ACCCATCCCC ACTTCACATC ATATGCCGTA TAGCCATGTG
     1510       1520       1530       1540       1550       1560       1570       1580       1590       1600
TCATTTTGCT GTGCCTGTGG CCCAGCAATC TCTAGGCTCT CCCAGGAGCT CCATCAGTGC TGCTTTGGAA AACGGGACAG GACTTTTTGC AGGTCTCTTG
     1610       1620       1630       1640       1650       1660       1670       1680       1690       1700
GCCCTGGGT GGGCTCCCTG CTCCTCCTGC CACCCACGCC ACTTCTCTCA CCTGGGATCT GGAGAGCAGT CTCTCCTGCC AGTCAAGAGT GGGGTGACCT
     1710       1720       1730       1740       1750       1760       1770       1780       1790       1800
TCCCCCACCA GGCAGAATCC ACCCCCTAGC CTAACCATGG CGGCAGCCAG CCTCTGGCAG CCTCTGCAGC CAGCTTGTCC CAGGGCTCTG CTCGTCCAGG
     1810       1820       1830       1840       1850       1860       1870       1880       1890       1900
TCAGCAGG TCCCAGGGGA GTCGGACCAG GGAGGGGCAT CTGCAGGAGG TGGGGGTCCT GAGAGTTCCC CAGGAGGGCG AGGGGACAT GGCGCACAGG
     1910       1920       1930       1940       1950       1960       1970       1980       1990       2000
TTATCAGTAA ATGTCATCGA GACTGTCCCC AGACACTCAC AGGGTGCCAG GCAGTCTCTC CTTTCACCCT TGCAAACCCT CCCCTGGGAG GTCGCCATCT
     2010       2020       2030       2040       2050       2060       2070       2080       2090       2100
GCTCGCGAG GCAGCAGGAG AGGACTGGCC AATGTCAAAG AGCCAGCCGG GAGCAGACCC CAAATCTCAG AGATGCTTCT GGGCCGGTCA CCCTCCACCA
     2110       2120       2130       2140       2150       2160       2170       2180       2190       2200
GGGCTCTGTG GGGCCCCACA TCCCACCCAA GTTGTCCCTC CCGGACCCAG GGGGCCCCTG GCTGGGAAGC CAGTGAGCCG AGAGGGCGCC AGAAAGAAGC
     2210       2220       2230       2240       2250       2260       2270       2280       2290       2300
TGGACCCTGC AGGGACGCTG GTCTGCACAG CCGTGCTAAG TTGCTTCTCT GTGGTGTCCC CACCCCGGCC AACCCCCAAC CCTCTCTTGC TTTTCCCATC
     2310       2320       2330       2340       2350       2360       2370       2380       2390       2400
TCTCACCAGG CATCAGCAGG TCCCAGAAAG ACCCCGACCC CAAAGGCCCT GTGGCACTTG CGGCCACGAG AGCCATGACA GGGCCCCCTA CTACTCCTGT
```

```
2410        2420       2430       2440       2450       2460       2470       2480       2490       2500
CCCCTCCACG  TCCACTGCCT GTGGCCCCCT ACTACTCCTG TCCCCTCCAC GTCCACTGCC TGCCCCCCAT GGCGCCCAGC ACCCCACAGC CACAGGTGGG
2510        2520       2530       2540       2550       2560       2570       2580       2590       2600
TGCCAGGGTA  CAGCGACCCC TGTCATCCCA CCCTCTCCTG GCTTCTAGCC TGGGTCCCTG GGTGGGAGGG TCGAGGCGAG CCCTGGGCAG
2610        2620       2630       2640       2650       2660       2670       2680       2690       2700
AGAGCAGGGG  CTTGGCTCTT AGAATAGAGA CGTAGAACC  CTAGAGGCTG GGAGCCACAG GCCAAAGGGG CTTGAGGACA CCTGGGTCAA CCTGTTCCTG
2710        2720       2730       2740       2750       2760       2770       2780       2790       2800
AGCCCTGCCA  GGGGATTCAG GGATCAGTTC AGCTTCCAAG ATCGTCTTCC TCCTGCCCTT CAAGCCATTG CTTGGAAGTG CTCCCAGACC ATTGTGGCCA
2810        2820       2830       2840       2850       2860       2870       2880       2890       2900
GACGGCTGCA  GGAACTGAGA GGAAAGGTGC TGGGGGCAGC GAGGCCATCC TGACATGCAG CCAAAGACTG GCCTTATCTC CCAATGGTGC TTCTGCCTCC
2910        2920       2930       2940       2950       2960       2970       2980       2990       3000
GTGGTCCCTG  GAGCCCCGCC CACACCCTGT CCCCAGGGCC TCTCTGTCCT TAGCCCCTCA GCAGCAACAC CGGTGGGATG GATGGAGCAG
3010        3020       3030       3040       3050       3060       3070       3080       3090       3100
GGTTAGCCCA  GAAAGCAAAT GTCTCTGATC AGCAGGGCAA AGGGAGCCTC TGGAGCTACG TTTGGACCAC CGTGGGCTGC TGGAATGTGG AGGCTGTGTG
3110        3120       3130       3140       3150       3160       3170       3180       3190       3200
TGTAGTGCAA  GGCCAGGCCA GGGCCAGACG TCCTGCCCCT CAGGGCCCTG CCACAGACAG GCATGGAAAC CTGATTCTCG CTCGCCCTCC AACGGAGGGA
3210        3220       3230       3240       3250       3260       3270       3280       3290       3300
TTCACGTGTA  TTCAAGGCTG GGGGTGCTGA GTGGGCCTCT GCTCTCACCT GGACTCACCT GGGGAGTATC CCACTCTGTG CAGTGCAGGT GCCAGGGGTC
3310        3320       3330       3340       3350       3360       3370       3380       3390       3400
TGAAAGGATT  TATCCTTCCA GAGGGCACCA GGAAGACGAT GACCAAGGGG GAATTCTTCC TGGTCCCAGC CAGGGAGGGG TGCTCCAATA GCCTGCCACA
3410        3420       3430       3440       3450       3460       3470       3480       3490       3500
CCCTGTCCCC  CGCCACCCTG CAGGGAGGAC CTGGTGGGGA CCTCTGGAGTG CCCTGGCCCT CCATCTCTCT GATCCAAGGA GACCTGCCCC
3510        3520       3530       3540       3550       3560       3570       3580       3590       3600
ACTGATCCTT  CCCCTTGGGT GGCATTTCTA AGGCAGAGTC CCTCTACAGC CCTCTGGCCC TGTTGCTGGT GGACATCAGG CTCCCAGACA GGCATAGCTG
```

```
      3610       3620       3630       3640       3650       3660       3670       3680       3690       3700
AGAGAAGACC TCCTCCTTCC TAGGCCATCC AGAGCAGCTC CCTGGGGCAG CACACCCAC CTCTTTCTAC ATCCTTCCTT TTCTGCAGAG CATTTACAGG
      3710       3720       3730       3740       3750       3760       3770       3780       3790       3800
AGGCATTTTC TAGCCAAAAG ATTGGAGGAT TTCCGGGAAG CCTCCTGACC CAGGAATCCT CTTTGGGGTG GAAGACATGG GTCACTCTGA GAATTCTGGA
      3810       3820       3830       3840       3850       3860       3870       3880       3890       3900
CTTCAAACAT AGGTTGGCCC AGCCACAAGG GACCTGTGCT TTGCTGATGA GCCTGTGGTG GGCAGACAGA AGCAAAAACA GTGGTGGTGG GTGCTGTGCC
      3910       3920       3930       3940       3950       3960       3970       3980       3990       4000
TGTCTCCAAA CAGGGTTTG GCTGGGAGGC CAGATACTCT TGTGCAAGTG CCATATCACA TGTGCAAGTG CACACATGCA CACATGCATG CACACACACA
      4010       4020       4030       4040       4050       4060       4070       4080       4090       4100
GGCATGCACA CGCACACATGTA CACACACACA AATCCATTTG CAGAGCTGCT TCTGACTTGG TGCCAGGGCC AGCCGTGGGA GGCTGGGCAG
      4110       4120       4130       4140       4150       4160       4170       4180       4190       4200
ATTGTGCAAG TTGGAATTA AAGAGGAAAA GTCAGAGGCC AGAGTGGGAA ATGCAGGGGA GTTGAGGGTC CCCAGGACCC TCAGTGAGCA GAAGGCACAC
      4210       4220       4230       4240       4250       4260       4270       4280       4290       4300
CCTCTCGGCA AGACAGTGCT GCTCTGCACC TAGCCCTGTA TCAAGAAGCA GGACATTAGG GGAGGAGGTG GCTCCAATGT GACAGCCAGT GGCCCCTACA
      4310       4320       4330       4340       4350       4360       4370       4380       4390       4400
GCCACATCTA GGGCTCCCTC CCTCCTCTTC AGCAACTGAA GCCCCTGTCC AGAGCCCCCA TTAATGAAAA CGATCATTGC AGTAGCTGAG GGTGAGTTCT
      4410       4420       4430       4440       4450       4460       4470       4480       4490       4500
CCTGGGCTGT GCTCGTATGA TTGTATCATC ATATCATTGT ATTCTGGGCT CACAGCTCCG TGAGATGGAG GCTGTTATTT TCCTAGTCCC ACAGGTGAGG
      4510       4520       4530       4540       4550       4560       4570       4580       4590       4600
CCTGGGCTGG TTAGGAAGAA GCAGCTGGAT TTTATGATAT GTAAAATTAC ACCTCAATCA AGCTGTTTCA GAAGAAAAAA GGGGCAGCTG CTCAAGGTCT
      4610       4620       4630       4640       4650       4660       4670       4680       4690       4700
GGATCGAGGC GAGAGGCACG GGCAGGATTT GAACTCAGGG CTGCCAACT CAGCCACCA AAGCTATTGT CCTGAGGCCT CCAGGGCTA TGAGGTAGAG
      4710       4720       4730       4740       4750       4760       4770       4780       4790       4800
CAGAATTATG GAGAGGCCTC TTTTTTTTTT TTGAGATGGA GTTCGCTCT TGTCGCTCAG GCTGGAGTGC AATGGAGCAA TCTCAGCTCA CTGCAACCTC CGCCCCCCA
CTATCTTTTT
```

FIG. ID

```
4810       4820       4830       4840       4850       4860       4870       4880       4890       4900
GGTTCAAGCA ATTCTCCTGC CTCAGCCTCC CGAGTAGCTG GGATTACAGG CACCTGTCAC CATGTTCAGC TACTTTTTGT CTTTTTAGAG AGACAGGGTT
4910       4920       4930       4940       4950       4960       4970       4980       4990       5000
TCACCATGTT GGTCAGGCTG GTGTTGAACT CCTGACCTCA AGTGATCCAG CCGCCTCAGC CTCCCAAAGT GCTGGGATTC CAGGCGTGAG CCACCGCACC
5010       5020       5030       5040       5050       5060       5070       5080       5090       5100
CGGCCAAGTA GTGCTGTCTC CAAGGCCTGG CTTGCAGGGC TTCCCAGTTC CAAAGGAGCA GACCGGGCTT CCATGGGGCC TGGCACAGC ACACAGGCCA
5110       5120       5130       5140       5150       5160       5170       5180       5190       5200
TGGCGAGAAC TTGCTTCCCA CACACCTGAG TGTGTCCCTG GGCAGCCAAA GCCAGGACTC CCTCCCTCCC CAAGACCCTG GTCCCTGAAA GATCCTGAAT
5210       5220       5230       5240       5250       5260       5270       5280       5290       5300
ACCCCGAGT GCCTCCCAAC AGGTGCTTCG ACAGAGTCCA GCCAGGACTC CCTCCCTCCC CAAGACCCTG GTCCCTGAAA GATCCTGAAT
```

FIG. 1F

```
       6010       6020       6030       6040       6050       6060       6070       6080       6090       6100
AGTCAGAACG GGGACGGGCA CAGGGAGTGT AGAAGGGTCT CGCTGAAGAA GTATGCAGAT TCTCAGGCGA TGGGTTCACC TCTCATCTAT CGGGCTTTAA
       6110       6120       6130       6140       6150       6160       6170       6180       6190       6200
GTCTGCATGT GCCCTCCACA GGCTAAATAG TGTAGATGCT GCCTATGTAG TAGATTTGGA CCCAATTCCT TTGGCCATGT AGACAGAGCC TCTCCTTATA
       6210       6220       6230       6240       6250       6260       6270       6280       6290       6300
GTGCTGCTGC TTCTAGGGGG CCTGTGGGTA GCGGGGCTGT GATGCCTCAG TATGTACCCA GCTTCCCTCA GCACCACCCC CTCGCATAAC TTGGTTTCTT
       6310       6320       6330       6340       6350       6360       6370       6380       6390       6400
CTCTTCTTCC CCCAAGAGT GGACCAGGCC ATCTACGGCT GCCCCTCT CGAGCAGGTG GTCCCAGGTG GCCTCCGTG CAGAAGGTAT GGGGGCAAG
       6410       6420       6430       6440       6450       6460       6470       6480       6490       6500
GCCTGTGATG GGCCTGAGAC CCCGGGAAGC GCCCTCTTAG ACTCGTAGCC CCTCCCTCTG TAGTGGAAGT AGCAGTGTGC ATGGTGGGAC CTAGTTGGAG
       6510       6520       6530       6540       6550       6560       6570       6580       6590       6600
GGGGGCCGCA GGAACCAACT GAGGGCACGG TGTAGAATGT CGGTGCCTGG GGCACAGTGG TGAGGGAGCG GCTGGTAGA GCAGGTCTAC
       6610       6620       6630       6640       6650       6660       6670       6680       6690       6700
CAGCTCTGCC CCCAAGCTCA GAGGTTCCAT GTGGCCACCC TGCCCTTGCT CCACGCCAAG CCCTTCCACC AGCACTCCCT CCGAGGGCTT CGGAGTCTGG
       6710       6720       6730       6740       6750       6760       6770       6780       6790       6800
TAGAGCCCCG CCTCCCACGA CAGGAACCCC CCTCTCCAGC TGCCCTTGCT CACAGGACAC CTGGGCCAGTT GCTGGATCAG AGAGTCAGAG GGGGCTTCCT
       6810       6820       6830       6840       6850       6860       6870       6880       6890       6900
GCAGGAGCGG GGGCCATGAG ACCTCGGAGG GTGGACTGTG GTGGGTGAAG GGAGAAGGCA GCACATTCCA GGCCGCAGGC AGCGGGGGCA AAGGCTTGGC
       6910       6920       6930       6940       6950       6960       6970       6980       6990       7000
AGTGGGATGG CAGGGAGCCT GACAAAGTGG AAAATGTGTG GGTTAAAGGA GGGAGGGCGG GGTCCTGGAA GACACTGACA TCCTCCTGCT ACGTGGGAGG
       7010       7020       7030       7040       7050       7060       7070       7080       7090       7100
AGACACAGGG CTCATCTGTA GCCATAGACA GACATGCCAA GGAAACGCGC AGGCCTGCCC GACTCTCCAG AAGGGAAATT GTCCCTGGCC CCAGCTCACC
       7110       7120       7130       7140       7150       7160       7170       7180       7190       7200
AAGCCTGGTC GGGCCAATTA GGGCCTAGTC TAGGGAACAG GTGAGCTGTT CCTTCCAGCT CACATGTTCA AATTTCCTCC AGCCCCAGCT CTGAGCAGCG
```

```
7210       7220       7230       7240       7250       7260       7270       7280       7290       7300
AGCCGGGCTT TGAGGCGCCCT CTACTGGCAG GAAGCTCTGG CGCTGGAAGC ATGTTTAGAG AGGGTCTGAG GCTCGGTTCC TAGAAACCTG GAGGACCTGG
7310       7320       7330       7340       7350       7360       7370       7380       7390       7400
GCCTGGTGTC CTCTGTGGTG ATGGAGACAG AGCTGGCGGG AGCCATCGCT TCCCTACCCT GGGCCAACCA GGGCACCACA GACCCAGAGG GAAGCCAAGG
7410       7420       7430       7440       7450       7460       7470       7480       7490       7500
TAGTGACGAT CCCGGGACAG TGGCCTGCTC ACCCACAGAT AGGGCGGTTGG GGTCCCAGCG GATTCTGGGC AGTGGAAGGC AGGTGCGTCC GTGTTCCTGG
7510       7520       7530       7540       7550       7560       7570       7580       7590       7600
CTTGACAGCA CTTGCGAGTG GGACTCCAGG GACAGCGAAG GGCTGGAGCA GGAAGAGTGT TTCAGAAAGG AAGGGAGATG CCAAAGTCCT
7610       7620       7630       7640       7650       7660       7670       7680       7690       7700
TAAATGCCAA GTTAGTCTC TGGGTTTGAT GCTCCAGGA GTTTGGAGAG GCGGTGGGGA GAGCAAGAGA CGGGCGTGGT GTGCAATGTG ATGTCAATCT
7710       7720       7730       7740       7750       7760       7770       7780       7790       7800
ATCTAAAAAC AGTTTGGCTT CCAAGAAGGT CTTAGCAGGG CGCGGGGGTG TCAGGGGTTA CAGAAGTCAT TTGAGATTAA TCCCAGCAGA TGTGTCATGT
7810       7820       7830       7840       7850       7860       7870       7880       7890       7900
CTCAGAGAGG GACCAAGGGC AGGGCTGATT TGCAAGCTTG GGATGTGCTG TGTTTCCTTC AGAAGGGTCC CACCTCCCTG GGCTCTTCGA GGAGAGGGGC
7910       7920       7930       7940       7950       7960       7970       7980       7990       8000
TGTGTGATTT GAGGCCAGAG GGGCCCTTCC CTCCCTCTCC CTGGCAGCTTG TCTGAGCAGG CGACAAGCTG CCTGCCCCA AGCTGGCCTAG GGGCGGCTCG GAAGCCTTTG
8010       8020       8030       8040       8050       8060       8070       8080       8090       8100
CTGGGCTCTT CCCTGCCCAG TGGGACCATG ACAGACGAAA GAACCTGTTT CTCATCTCTC CAAGCTGTGG GCACCCCTGC CGCTGCCCCT GCCCCTGCCA
8110       8120       8130       8140       8150       8160       8170       8180       8190       8200
AGGGCTACAA ACTTTTCCAG CTCAAGCCCA AATCTCCTCA AGTGATGCCT ATTGAAGAAT TCCAAGGTAA GAGGATGGAC CTGGGGCCCC ATCAGCCCTC
8210       8220       8230       8240       8250       8260       8270       8280       8290       8300
CCTGACACCT GTTCCCCATC CGCCGGCTGGA AAAAGAGCGGA GCAGGATAGA GGACCGATGC CTGGCTCGA AAACCCTCCT GGAGTAGCTG GGTCAAGGTT
8310       8320       8330       8340       8350       8360       8370       8380       8390       8400
AAACTGAGTC TCTCCTCCCT ACAGGCCTTC CTCCCCAAGG GAGCTGGGAG CAGGTATGAG TCAGAAGCCA CAGGGCTAG AGTGGGCAC GCCACACAGC
```

FIG. IG

```
8410       8420       8430       8440       8450       8460       8470       8480       8490       8500
AGGCAGAGCA GATGCCAGAA ATAGCCCATC CCGGCTTCCC TGGGAGGTGT GGCCCTGGGG CTTGGTTGTG TCTAAGCAGA ATCTGGACAC ACGGTCACCA
8510       8520       8530       8540       8550       8560       8570       8580       8590       8600
TGCTGCTCTT GGACACTATA GGATGCCTCA TCTCCTCATT ATCTCTGGAG GGACAAAGTG AAGGGGGCAG GACTAGTGGA CAGTGGGATG CCCACCATCT
8610       8620       8630       8640       8650       8660       8670       8680       8690       8700
CTCCTGGGCA CAGGCTGTTT CTCTAGTCTC CCAATGCCCT TGACCACTGG GTCAGTCCCT CATCCCATCA CAAAAGGGAA GCTGGGTCCT CTAGAGATAC
8710       8720       8730       8740       8750       8760       8770       8780       8790       8800
ACAGATGGTG TTTCAAGAGG GTGGCCGTTG TCCTTCCTTG TTCGGGGGCA GCCACATTGG CTTTCTTGCT GGAGGGTGGG TGGGTGGGTG AGTACTGTGT
8810       8820       8830       8840       8850       8860       8870       8880       8890       8900
CCCTTCGTAG AACATCAAGG ATGCCCCCCC ATTCTTTAGG ATGTGACCTT CCTCACCAAA TCCTCCATTG ACAATGTGGG ATTCACCTCC AATCCCCTGA
8910       8920       8930       8940       8950       8960       8970       8980       8990       9000
GAGAGCCTGG CCCCAGGCAG TCACGGGCTT GTCTGGTCCT TGGAGCGGAG CTGGTTAGGC AGGGGTCAGC CTGAGAACCA CGTAGGGGTG GGGTGCAGGA
9010       9020       9030       9040       9050       9060       9070       9080       9090       9100
GGCGGCAGGA CATGGTGGTG GTGGTCCTTG GTATGAAACC AGTGCTTCC AGGAGCAGCG AGTCAGAAGC CGGGCCAGGA CCAGGGGGAG GCATGCAGGT
9110       9120       9130       9140       9150       9160       9170       9180       9190       9200
TCCCAGGGCT CCTGCTTTAA AGTGGCACTC ACTCTTAGCA TCCTGCAAAT CAATCAAACT TGCACAAAGC TCAGGCTAAT AAGAAAGGGT CTGGCAGGTG
9210       9220       9230       9240       9250       9260       9270       9280       9290       9300
GGGTTTTCC TCCCAGCCAT CTTCCAAAGC AGCATGGGCA GGAGCTCCTG GCCCATTGCA TCTTGTCCAG CGTCCATCCA TGCATTCATC TACCCGAGGA
9310       9320       9330       9340       9350       9360       9370       9380       9390       9400
TACCACGGCG AGCGCCGTGA ACCCAGGGGT CGCCTCCCCC AGTGCACAGC CAGGTGGCAT GACCCGTTCC TCCTTGCATG AATCACTTTC TAATCACCCC
9410       9420       9430       9440       9450       9460       9470       9480       9490       9500
GGCATGTGGG CATTCCTTCA ACCCAGGCTT GCGAGGCGCTT CCCAGGGTG CATTAGCAGG AGCTGCCCAT GGCCCTGCCT GGTTCCCTGG GGACAGGCAG
9510       9520       9530       9540       9550       9560       9570       9580       9590       9600
GTGGGAATCC TGGGCTAGCT ACTCAGGTTC TCCTCTGGGC GGCCCTGGTG TCAAAGCAGG GAGGCCTCTC TCTTCCTGAA TCCGATGGCA AGGGTGGGAG GCCTAGGGCA
```

FIG. 1H

```
      9610       9620       9630       9640       9650       9660       9670       9680       9690       9700
CCTTCCGGTA AGATGCCTTC CTCCTGCCCT GCATGACCTG GGGTGAGTCC TTCCTCGCCC TGTCCCTCAG TTTCCTGAAT GCTGCTGAC 9710       9720       9730       9740       9750       9760       9770       9780       9790       9800
CATTGGTATT TCTCCCACTT GGCCGGCCCA GACTGCGAAT GCTACGGTCA CTCCAACCGC TGCAGCTACA TTGACTTCCT TGAATGTGGT GACCTGCGTC 9810       9820       9830       9840       9850       9860       9870       9880       9890       9900
AGCTGCAAGC ACAACACGCG AGGTCAGCAC TGCCAGCACT GCCGGCTGGG CTACTACCGC AACGGCTCGG CACAACTGGA TGATGAGAAC GTCTGCATTG 9910       9920       9930       9940       9950       9960       9970       9980       9990      10000
GTTGAGAGGG CACGGACACG GCACAGGGAA CTTGCTGGAA TGGTGCAGG GTGCACTGCC CTGCGAGGTG GCCTCTGGGG GCCCCCTGCA TCAGAATCAC 10010      10020      10030      10040      10050      10060      10070      10080      10090      10100
CTGGGGAGAC TGTGGGAATT CTAACTCCAG GGCCCTCTCC AGTTGAGCAT CTCTAAGGAC AGAAAGCTCC AGAAACTGCT CTATTAGTAA CCTACCCTTG 10110      10120      10130      10140      10150      10160      10170      10180      10190      10200
CGGTTCTCCG GTAAGTTTTG CACTGGAGTT GCAAAACTTA CCAGTGGCCC TTCCCTCTCT GGGCAACTGG AGGGGACACT GACCCCTCTG GCTCAAAGAG 10210      10220      10230      10240      10250      10260      10270      10280      10290      10300
CTGTGACTCT GGCAGGTGGC AGGCGGACTCA TGGCAGAGGC CACTGAGCAT CTGGTGTGTG GGGGGGTCCCC CTCCATAGCT CCTTTTCCAGA 10310      10320      10330      10340      10350      10360      10370      10380      10390      10400
AAGTGGAGG AGCAGCCTAT CCCTCCTCCT GCAGGGGGCC AGTTGGGGCT AAAAGATCGC CTTGCTGCGT GCATTTGTGC AAGTCCCTTC CCGTTGCTGG 10410      10420      10430      10440      10450      10460      10470      10480      10490      10500
GCCTCAGCTT CCTCATTCAT CAAATTGGGA GGCAGATCAG ATCAAAGGTT TTCAGCTCTT TTTTGTGGCT GAAGCTTTTC TTCAAATGCT TTACCAGCCC 10510      10520      10530      10540      10550      10560      10570      10580      10590      10600
AGGTCCAGCT ATAAAGCTT TCTTCACCCG TGGTGGGCAC CCAGTCTGCT TTCTTCCAAG TTGCTACTCA AGGACTGGCT TCTGGGTAGA GAAGGAAGTC 10610      10620      10630      10640      10650      10660      10670      10680      10690      10700
CATCAGGGCC CTGGGCTGGG CAAAGACCCA AAGCCATGAC CGCCAACCAA ACGCACAGCT GGAATGGTTG CCCTGTCGTC AGTAGAGGCC AGGTCTCGGC 10710      10720      10730      10740      10750      10760      10770      10780      10790      10800
CTCAGGGCT GTCCCCAAC CCTGCCCAGC CAGGCCCTTG GGACACCATC ACCCATCCCC CACCCAGCAG GAGGCTCTGG CTGCCCAGAG GAGGGCTCC
```

```
         10810      10820      10830      10840      10850      10860      10870      10880      10890      10900
TGCAAAGCTG GAGCTGTCGG TCTGAATTCT GGGCGGCCATG TCAGATAATT CCATCAACTC TAAGTGATCA AAGCCGCTGA CGTCACAGGG GGCCAGCTGC
         10910      10920      10930      10940      10950      10960      10970      10980      10990      11000
AGGGACAGGG CAGGGCCTTT GGATCCAATT AGAGGTGCCC ACACCCTGGC ACCCTCCTCC TCTCCCTGGC TCTCCCTGCC TCCACCCCGA GAGCCAGCAC
         11010      11020      11030      11040      11050      11060      11070      11080      11090      11100
TGAGCTGCAA GGTTTCTCAG GGTGGACGAT ATTCACCCTC TCCCACAGAG CCCCAAGGCA ACCAACTGGG CCCACCCGGG AGCAGGAATA GGCTGTTCCT
         11110      11120      11130      11140      11150      11160      11170      11180      11190      11200
CCACGTCCCC TGCAAAGGAG CTATGGAGGG GGGCCACCCA CAACACAGCA GCCCCAGAGA TGCTCAGTGG CCTCTGCTGA GTTTCTGCCA CTGTCGGAGT
         11210      11220      11230      11240      11250      11260      11270      11280      11290      11300
CATAGCTCTT TGGAGATGGG AAGGACAGCG ACCCTCTAGT TGCCCAGTGT GGGGAAGGGG CTGACCAGGC CACACCAGTG CCAGGGCGGG GAAGGTGGGG
         11310      11320      11330      11340      11350      11360      11370      11380      11390      11400
CTGGACGTG TTTGATCCCA AGGAAGGAAG CCAGAGTCTT CTCTCCAGGC CTGGCCACCC TGGGAAGTCC CCAACCTGCCG GGCTCACGTG
         11410      11420      11430      11440      11450      11460      11470      11480      11490      11500
GACCCAGTGT GGGGAGCATC CCCTGGGGAG TGTGGAGATG CTCCCTGCGA GGCGGGAGA GTGGGGTCC GAGCAAGACG GCGCCCACAC GTAGCCCTGA
         11510      11520      11530      11540      11550      11560      11570      11580      11590      11600
CCGGCGCCC GTGCCGTGT CCGTCCAGAG TGTAACTGCA ACCAGATAGG CTCCGTGCAC GACCGGTGCA ACGAGACCGG CTTCTGCGAG TGCCGCGAGG
         11610      11620      11630      11640      11650      11660      11670      11680      11690      11700
GCGGCGCCG CCCCAAGTGC GACGACTGCC TCCCAGCGAC TACTGCGCA GGGCTGCTAC GTGAGTGCGG GCGTCCCCG TGGCGGGCCT CGGAAAGGGG
         11710      11720      11730      11740      11750      11760      11770      11780      11790      11800
AGGGCTAGA CCAGGCATGG CGGCCTATGG CGGGCCAGGC GTGGCATGGT CTAGCAAGCA GGGCAGGCCG GGAATGGTGG GCCTATGGCA GGGCAAGAGG
         11810      11820      11830      11840      11850      11860      11870      11880      11890      11900
CTGGGGGGG CCTCGGAGA CGGGAGCAGGC CAGGGCAATGG TGGGCCTAGT GAGACGGGCA AGGTTGGGAT AGTTGGCAGG GGCCTGGTGA GATGGGACCG
         11910      11920      11930      11940      11950      11960      11970      11980      11990      12000
CGTGGGGGG CCTCGGAGA CTCTAGCGAG ACGGAGCTGG CAGGTGGGCG GGGACAGGAT GCTGCTGAGG GCTGGGGCAC TCCGGGCAGG GGGCCGAGGG GCGGGTCCAA
```

```
12010      12020      12030      12040      12050      12060      12070      12080      12090      12100
GAGCTCGGGG CGGGGCCTGA TGCGACCTGA GCACGGGTGGT GCCTGGTGGG AACTACGAGA AAGACCGAGC TGGGGTTGGA AAGGTATTTG CGGGGACAGA 12110      12120      12130      12140      12150      12160      12170      12180      12190      12200
GGGAGGGAGG CTGTCCAAGT CGGCGTTAGC CGCGGGCACA GGGTGAAAGG AGGCTCCAGG CGCGTGGAAC AGCACGTGCA CAGCTCTGGA GACTGCAGGC 12210      12220      12230      12240      12250      12260      12270      12280      12290      12300
GCGTCTGAAG AACAGCACCG AGGGGGAGA GGGGGGCAGC GGTGGGCAGC ACCGGGGAGGC CGGGGGGGCC AGATCTCGCC CGGGGCGCCGT CACCCTTCGA 12310      12320      12330      12340      12350      12360      12370      12380      12390      12400
GGGGACGT TTCGCACCCA AGCCTCCTAC ATCCCCGGGC CAGACGGCGC CCCGGGGGTC TCGCACACCC TGTTCGAGAG CTCGGAGGTT 12410      12420      12430      12440      12450      12460      12470      12480      12490      12500
GGCGGGGGA CCGGGCCACC GCGCGTGCTG ACCGCCCCT CCTGCAGCCA ACGTGTGCGA CGACGACCAG CTGCTGTGCC AGAACGGAGG CACCTGCCTG 12510      12520      12530      12540      12550      12560      12570      12580      12590      12600
CAGAACCAGC GCTGCGCCTC CCCGCGCGGC TACACCGGGC TGCGCTGCGA GCCAGCCCCG CTGCGACCCC GCCGACGATG ACGGCGTCTG GACTGCGACC 12610      12620      12630      12640      12650      12660      12670      12680      12690      12700
GCGCGCCGG GGCCGCCCCC CGGCCCGCG GCTGCTCCG GCTGCCTGCT GCGCGACCCG CTGGGCGGG CTGGGCCGC GCCGAGGATGC CCGGAGGAGT 12710      12720      12730      12740      12750      12760      12770      12780      12790      12800
CCCGCACCG GAGGCCGGGG TCCCGGAGGC CAGTCGAGGG CGGCGGCCGG CGGGCTGAGG AAGGGTGCGG CCCGAGGTGC TCCCAGGTGC TACTCAGCAG 12810      12820      12830      12840      12850      12860      12870      12880      12890      12900
CCCCCCGC CCGGCCGGCG CACTGCCCTC CCCCGCCCCG AGGGCGGCCT TGGGACTCCG GTCCCCCAG CCTGCGATTT GGTTTCGTTT 12910      12920      12930      12940      12950      12960      12970      12980      12990      13000
TTCTTTTGTA TTATCCGCCG CCCAGTTCCT TTTTTGTCTT TCTCTCTCTC TCTTTTTTTT TTTTTTTTC TGGGGTTGAG CAGAGGGTCG GGAGAAACGC 13010      13020      13030      13040      13050      13060      13070      13080      13090      13100
CCCCCACCC ACACCCGTCC TGCCTCCCAG CACACTTACA CACCGGGAC ACCCCTGGCC TGTGCCAGGC TCACGGCAGG CGGCGGACCC 13110      13120      13130      13140      13150      13160      13170      13180      13190      13200
TGCTCGCCC ACACCGTCC TCCTAGCGCT GACTGTCCT GTTTCTATTC TTATTTTCCT GCAACCACC ACACCCCAGG CCTACCGCAG GGCCGGTGA
```

FIG. 1K

```
13210      13220           13230           13240           13250           13260           13270           13280           13290           13300
CCACGCAACT CACCCTGTGG GAGGAGGAGA GAAGCAAGGG GTGGGGGGCC CTGGAAATTC GCTTCTGTAG AGAATCTTTT TGTTTGTATT CACTGTCCTG 13310      13320           13330           13340           13350           13360           13370           13380           13390           13400
CAAGGGGGAC GGGCAGGACT GGTCAGCCGC GGGGGCCGAT GGTGGAGAAT CCGAGGAAGT AAAGAGGTTT GCTCACTGCT GCCTCCACGG CCTGTTTTCT 13410      13420           13430           13440           13450           13460           13470           13480           13490           13500
TTCTGTGTTG GGCACGGTGG GCAGGTGTGG GGCTTACAGA GGAATCCACA ACACAGCCTT AAAGAAACGT TTCCTACTGG GGCCACCATT TCCCTGGGCC 13510      13520           13530           13540           13550           13560           13570           13580           13590           13600
TTTCTGTGGA TTCCAGCAGC AGTGCCCCCT CCCCGCAGGC TTGGCTGGCA GAGTTTTCCA CCCCGCGGCC AGGCTGCAGG TGCCCACCT GTTAGGACCC 13610      13620           13630           13640           13650           13660           13670           13680           13690           13700
TCCCCACACT GAAAGGCTGC CTCCCTCCTT TCCCAAAAAA GAAATCCGGA GTGTATTGGC CCTTTTCTAC AAGAAGTCCA AGGGAAATGA CTCAGGGAGA 13710      13720           13730           13740           13750           13760           13770           13780           13790           13800
ATCCTAGCAG AGCTTGAATC CAATGCTCTG ATTTATACTG TGTCTCGGTG GCCACCTCCG ATGGATGTGT CATCTCAGAC CTGTTGCAGC CGGAGCCTCA 13810      13820           13830           13840           13850           13860           13870
AGTCCAATAT CAGATGAAGC TGAACCCACA ATGTCGGCCA CCGCCTCCTT CCGAGATTTC AGATGGCATG AATTC
```

METHOD OF PRODUCING A CELL CARRYING AN EXCESS OF MAMMALIAN CENTROMERES

This application is a continuation of application Ser. No. 08/080,097, filed Jun. 23, 1993, (abandoned), which is a continuation of Ser. No. 07/892,487 (abandoned) filed Jun. 3, 1992, which is a continuation of Ser. No. 07/521,073 (abandoned) filed May 9, 1990.

BACKGROUND OF THE INVENTION

The centromere is a specialized region of the eukaryotic chromosome. It is the site of kinetochore formation, a structure which allows the precise segregation of chromosomes during cell division. In addition to this, a possible structural role in the higher-order organization of eukaryotic chromosomes has also been suggested (Hadlaczky (1985), Internatl. Rev., 94:57–76).

The isolation and cloning of centromeres is crucial, not only to understanding their molecular structure and function, but also for the construction of stable artificial chromosomes. Taking advantage of the existence of centromere-linked genes, functional centromeres of lower eukaryotes (yeast) have been successfully isolated (Blackburn, et al. (1984) Ann. Rev. Biochem., 53:163–194; Clarke, et al. (1985), Ann. Rev. Genet., 19:29–56). The combination of a functional centromere with telomeres, which stabilize the chromosome ends, permitted the construction of yeast artificial chromosomes (Murray, et al. (1983) Nature, 305:189–193; Burke, et al. (1987), Science, 236:806–812). This initiated a new era in the study of chromosome function and in genetic manipulation.

Higher eukaryotes (e.g., mammals), in contrast to yeast, contain repetitive DNA sequences which form a boundary at both sides of the centromere. This highly repetitive DNA interacting with certain proteins, especially in animal chromosomes, creates a genetically inactive zone (heterochromatin) around the centromere. This pericentric heterochromatin keeps any selectable marker gene at a considerable distance, and thus repetitive DNA prevents the isolation of centromeric sequences by chromosome "walking."

Thus there is a need in the art for methods of isolating higher eukaryotic centromeric DNA. Isolation of such DNA is necessary for construction of artificial mammalian chromosomes. Use of such chromosomes could overcome problems inherent in present techniques for introduction of genes to mammalian cells, including the concomitant creation of insertional mutations, size limitations on introduced DNA, and imperfect segregation of plasmid vectors.

SUMMARY OF THE INVENTION

It is an object of the present invention to provide a method for isolating centromeric DNA from a mammal.

It is another object of the invention to provide a DNA element which will insure faithful segregation of inserted DNA in meiosis and mitosis.

It is yet another object of the invention to provide a DNA element for formation of vectors to insert large amounts of DNA into mammalian cells.

It is still another object of the invention to provide a DNA element which binds mammalian centromere proteins.

These and other objects are provided by one or more of the embodiments described below.

In one embodiment a non-human cell line is provided that contains an excess of centromeres.

In another embodiment a nucleic acid probe is provided which hybridizes to a DNA molecule having the sequence shown in FIG. 1.

In yet another embodiment a method of isolating centromeric DNA from a mammal is provided comprising:

isolating metaphase chromosomes of a mammalian cell line;

fragmenting the chromosomes to form a suspension containing chromosome fragments;

incubating the suspension with human serum containing anti-centromere antibodies to bind chromosome fragments to the antibodies;

separating antibody-bound chromosome fragments from the suspension; and deproteinizing said bound fragments to provide a preparation of centromeric DNA.

In still another embodiment a method is provided of producing a cell carrying an excess of mammalian centromeres, comprising:

cotransfecting cells with: (1) DNA carrying mammalian centromeric DNA; and (2) DNA carrying a dominant selectable marker;

selecting cells which express the dominant selectable marker;

detecting cells which carry an excess of mammalian centromeres.

These and other embodiments will be described in more detail below. The present invention thus provides the art with methods to access and isolate the important centromeric DNA of mammalian cells. In particular, a human DNA fragment CM8 is provided which can be used to create artificial chromosomes for gene therapy.

BRIEF DESCRIPTION OF THE DRAWINGS

FIG. 1 provides the sequence of a 13,863 bp fragment of DNA identified in a λ Charon 4A human genomic library.

Lanes A and B: DNA isolated from chromosome fragments remaining unbound to anti-centromere Sepharose.

Lanes C and D: DNA isolated from chromosome fragments bound to anti-centromere Sepharose. Note the presence of a population of high molecular weight DNA fragments. Samples of lanes B and D were treated with 100 µg/ml RNase-A prior to electrophoresis.

Lane M: λ HindIII marker.

Figure 3:
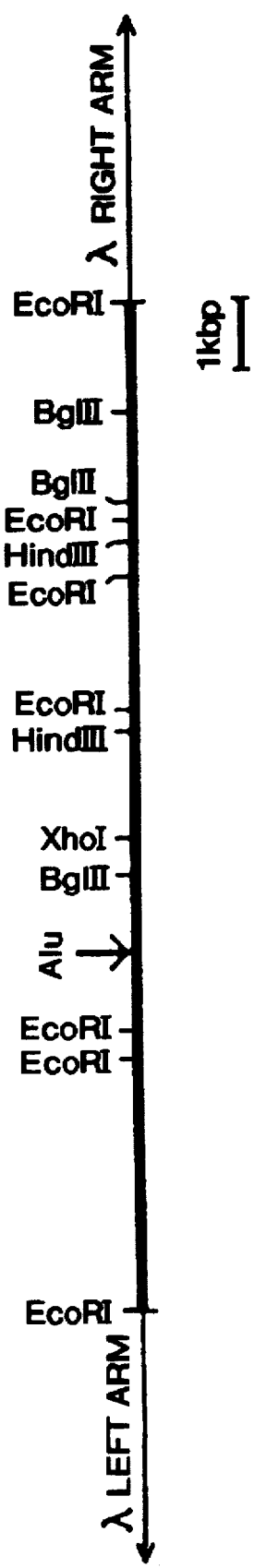

FIG. 3 shows a restriction map of the human genomic DNA insert of CM8 λ Charon 4A clone. The arrow shows the position of a 300 bp Alu repeat deficient in the flanking direct repeat sequences.

FIG. 4 shows the results of in situ hybridization with $^3$H-thymidine labelled CM8 DNA to human metaphase chromosomes.

Panel A: Preferential localization of silver grains at the centromeres of human chromosomes (arrowheads).

Panel B: Diagram showing the distribution of silver grains (●) on 131 metacentric chromosomes. Numbers indicate the frequency of silver grain localization to certain regions of the chromosomes.

FIG. 5 shows the detection of dicentric and minichromosome of the EC3/7 cells by indirect immunofluorescence (panels A and B) with anti-centromere antibodies, and by in situ hybridization with biotin labelled CM8 probes (panel C) and with a 1 kb SmaI/BglII fragment of APH-II gene (panel D).

Panels E and F: DNA staining with Hoechst 33258;

Panels G and H: DNA staining with propidium iodide. Panels E–H correspond to A–D, respectively. Arrowheads point to dicentric and minichromosomes.

FIG. 6 shows the duplication of the extra centromere in the EC3/7 cell line.

Panels A–C: In situ hybridization with biotin labelled CM8 probe.

Panels D–F: Corresponding DNA staining of A–C, respectively.

FIG. 7 demonstrates the colocalization of the integrated DNA sequences with the centromere region detected by immunostaining with anti-centromere serum (Panels A and D) and subsequent in situ hybridization with biotin labelled CM8 (panel B) and APH-II probe (panel E) on the same metaphases of the EC3/7 cells.

Panels C and F: DNA staining.

DETAILED DESCRIPTION

It is the discovery of the present invention that a segment of human DNA can be isolated and introduced into mouse cells and result in a a functional centromere. The functional centromeres containing DNA of the present invention are preferably linked to a dominant selectable marker. This can be a resistance marker, such as the aminoglycoside-3' phosphotransferase-II which provides resistance to G418 (Sigma). Other such markers known in the art may be used.

The method of isolating centromeric DNA of the present invention can be applied to any higher eukaryote, especially mammals. Preferably a human cell line will be employed. Metaphase chromosomes are isolated according to techniques known in the art. The chromosomes are then fragmented. Endonuclease digestion and mechanical shearing can be used to fragment the chromosomes. Desirably the majority of the fragments will be in the size range of less than 1 μm and some chromosomes will remain unbroken. Unbroken chromosomes can be readily removed from the preparation by centrifugation at about 1,500 g for about 10 minutes.

A human serum containing anti-centromere autoantibodies can be employed in the method of the invention. This is available from patients with CREST syndrome. Alternative sources of antibody may be used, such as monoclonal or animal derived polyclonal sera containing anti-centromere antibodies. The antibodies are incubated with the preparation of chromosome fragments under conditions where antibody-antigen complexes form and are stable. It is convenient if the antibodies are bound to a solid support. Preferably a support such as Protein-A Sepharose CL4B (Pharmacia) is used to facilitate separation of bound from unbound chromosomal fragments. However other methods to accomplish this goal can be used, as are known in the art, without employing an antibody bound to a solid support.

The DNA fragments comprising centromere DNA are liberated from the antibodies and centromeric proteins by a deproteinization treatment. Ultimately the DNA is purified from all proteins, by degrading the proteins and extracting them from the chromosome fragment preparation. Any such treatment known in the art may be used including but not limited to proteases and organic solvents such as proteinase K and phenol.

The centromeric DNA fragments can be used for any purpose or application known in the art. For example, they can be labelled and used as probes; they can be ligated to vectors to clone or all part of the sequences; and they can be used to purify centromeric proteins by attachment to a solid support.

In one particular embodiment of the invention the centromeric DNA fragments are used to probe a library of genomic DNA from humans or other mammals for clones which hybridize. Hybridizing clones can be analyzed for their ability to perform functions which centromeric DNA possesses. One such function is to bind to centromeric proteins. Another such function is to form a structure in cells which can be cytologically detected using appropriate immunostaining with anti-centromere antibodies which particularly stain centromeres.

According to another method of the present invention a cell carrying an excess of mammalian centromeres is formed. The cell may be human or other mammalian. The centromere may comprise DNA isolated from the same or a different mammalian species as the cell. The method involves cotransfection of a cell with two DNA molecules: one is a DNA carrying centromeric DNA; the other is a DNA carrying a dominant selectable marker. Preferably these two DNA molecules contain sequences which allow concatamer formation, for example phage DNAs such as λ phage. The first DNA molecule may be isolated from a library of genomic DNA using, for example, as a probe the centromeric fragments taught above. Alternatively the first DNA molecule may result from cloning the centromeric fragments taught above into a phage, for example λ, after manipulations to create fragments of the appropriate sizes and termini. The second DNA molecule is readily within the reach of those of skill in the art, for example a λ phage carrying a drug resistance marker.

It is believed to be desirable to employ λ phage DNA because it concatemerizes, however the absolute necessity of this has not been determined. Further, even if this property is necessary, other viral DNAs or DNA constructs may be able to supply this junction. Such other means of achieving concatemerization are also contemplated within this method.

After cotransfection, cells are selected which express the dominant selectable marker, for example by growth in amounts of G418 which are cytotoxic for the cells without the marker. This selected population of cells is further screened to detect cells with an excess of mammalian centromeres. This screening can be done by standard cytogenetic techniques, as well as by immunostaining with anti-centromere antibodies. Desirably the lambda, marker, and centromeric DNA (from the λ clone) will all be localized at the site of the extra centromere. This can be determined by in situ hybridization studies, which are well known in the art.

One cell line made by the methods described above is EC3/7 which has been deposited at the European Collection of Animal Cell Cultures, Porton Down, U.K. under accession no. 90051001, on May 10, 1990, under the conditions of the Budapest Treaty.

The sequence of the DNA insert in the lambda phage which was used to make the EC3/7 cell line, (referred to as CM8) was determined by standard techniques and is shown in FIG. 1. The sequence does not correspond to any in DNA sequence banks.

The present invention also contemplates nucleic acid probes, preferably of at least 10 nucleotides, which hybridize to a DNA molecule having the sequence shown in FIG. 1. One such molecule is CM8, the lambda phage clone from which the sequence was derived. Probes can be radiolabeled, biotin labeled or even unlabeled, for example, depending on the use for which they are desired.

The following examples do not limit the invention to the particular embodiments described, but are presented to particularly describe certain ways in which the invention may be practiced.

EXAMPLE 1

This example demonstrates the isolation of human DNA from centromeres.

Human colon carcinoma cell line (Colo 320) was grown as a stispension in RPMI medium supplemented with 10% foetal calf serum (FCS). Metaphase chromosomes of Colo 320 cells were isolated by our standard method (Hadlaczky, et al. (1982), Chromosomes, 86:643–659). Isolated metaphase chromosomes were resuspended in 1 ml of buffer (105 mM NaCl, 50 mM Tris-HCl pH 7.5, 10 mM $MgCl_2$, 5 mM 2-mereaptoethanol) at a concentration of 1 mg/ml DNA and digested with 500 u EcoRI restriction endonuclease for 1 h. The suspension was diluted with 4 ml of IPP buffer (500 mM NaCl, 10 mM Tris-HCl, 0.5% NP-40, pH 8.0) and sonicated for 5×50 s with an MSE 5-70 sonicator. This treatment resulted in a suspension containing chromosome fragments and a few ($\leq 1\%$) unbroken small chromosomes. The suspension was centrifuged at 1500 g for 10 min to remove unbroken chromosome fragments. The supernatant contained only small ($\leq\_1$ μm) chromosome fragments as judged by light microscopy.

Two hundred fifty mg of Protein-A Sepharose CL4B (Pharmacia) was swollen in IPP buffer and incubated with 500 μl human anti-centromere serum LU851 (Hadlaczky, et al. (1989), Chromosoma, 97:282–288) diluted 20-fold with IPP buffer. Suspension of sonicated chromosome fragments (5 ml) was mixed with anti-centromere Sepharose (1 ml) and incubated at room temperature for 2 h with gentle rolling. After 3 subsequent washes with 25 ml IPP buffer the Sepharose was centrifuged at 200g for 10 min.

Isolation of DNA from the immunoprecipitate was carried out by Proteinase-K treatment (Merck, 100 μg/ml) in 10 mM Tris-HCl, 2.5 mM EDTA,. pH 8.0 containing 1% SDS, at 50° C. overnight, followed by repeated phenol extractions and precipitation with isopropanol. All general DNA manipulations were done according to (Maniatis, et al. (1982) Molecular Cloning—A Laboratory Manual (Cold Spring Harbor Laboratory, Cold Spring Harbor, N.Y.).

Figure 2:
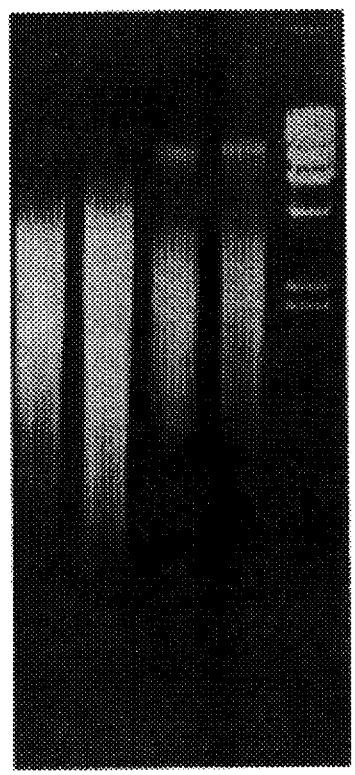
FIG. 2 shows the results of agarose gel electrophoresis of DNA fragments obtained by immunoprecipitation.

Results of electrophoresis of immunoprecipitated and supernatant DNA are shown in FIG. 2. The bulk of DNA from chromosome fragments which did not bind to the anti-centromere Sepharose (supernatant) ranged from several hundred base pairs to 5 kb (FIG. 2, lanes A and B), while DNA from chromosome fragments which bound to the anti-centromere Sepharose contained an additional population of high molecular weight (9–20 kb) fragments (FIG. 2, lanes C and D). This distribution of fragments sizes is conslstent with the notion that the centromeric DNA is in the structurally most stable region of mammalian chromosomes (Hadlaczky, et al. (1981), Chromosoma, 81:557–567), thus rendering this DNA relatively resistant to enzymetic digestion and mechanical shearing.

EXAMPLE 2

This example demonstrates the use of the high molecular weight immunoprecipitated DNA as a hybridization probe to screen a genomic DNA library.

The high molecular weight DNA was isolated from the agarose gel described in Example 1, by electroelution, labelled with $^{32}$P-dATP by random oligonucleotide priming (Feinberg, et al. (1983), Anal. Biochem., 132:6–13) and used as a probe for screening a λ Charon 4A human genomic library (Maniatis, et al. (1978), Cell, 15: 687–701). A hybridizing clone (CM8) was obtained which contains a 14 kb human DNA insert. The restriction map of this insert for some restriction endonucleases is shown in FIG. 3. Southern hybridization of parts of the 14 kb insert to human lymphocytic genomic DNA indicates that the 14 kb insert represents a continuous piece of DNA in the genome and is not the ligation product of a number of fragments.

EXAMPLE 3

This example demonstrates that the copy number of the 14 kb insert of clone CM8 is consistent with it being present on each chromosome in the human genome.

Southern blotting experiments were performed in which a single copy DNA probe (XV2C) (Estivill, et al. (1987), Nature, 326:840–845) and the central XhoI-EcoRI fragment of the CM8 insert (FIG. 2) simultaneously hybridized with serial dilutions of human peripheral lymphocyte DNA. The probes were labelled by random oligonucleotide priming (Feinberg, et al. (1983), Anal. Blochem., 132:6–13). By comparing the signal of the CM8 probe to the known single copy probe, the copy number of CM8 was estimated to be 16–32 per haploid genome.

EXAMPLE 4

This example shows the use of the CM8 DNA as a probe to human metephase chromosomes.

Radioactive in situ hybridization with $^3$H-thymidine labelled CM8 DNA to human (Colo 320) metaphase chromosomes was performed according to the method of Pinkel, et al. (1986), Proc. Natl. Acad. Sci. USA, 83:2934–2938. A preferential centromeric localization of silver grains was observed (FIG. 4).

In non-radioactive in situ hybridization according to the method of (Graham, et al. (1973), Virology, 52:456–467), using biotin-labelled subfragments or the whole CM8 insert it was not possible to detect a positive hybridization signal by our standard method. Furthermore, using a hybridization method which is suitable for single copy gene detection with a biotin-labelled probe (Lawrence, et al. (1988), Cell, 52:51–61), apart from the typical R-band like Alu hybridization pattern (Korenberg, et al. (1988), Cell, 53:391–400), no specific hybridization signal was detected on any of the chromosomes with the whole 14 kb CM8 insert. Possible explanations for this negative result are that these sequences are virtually inaccessible to the hybridization probe, due to their compact packing in the midst of the centromere structure, and that the biotin system is less sensitive than the radioactive one.

EXAMPLE 5

This example discloses the sequence of the human CM8 clone.

The sequence of the human genomic insert of λ CM8 was determined using the dideoxy method (Sanger, et al. 1980), J. Mol. Biol., 143:161–178; Biggin, et al. (1983), Proc. Natl. Acad. Sci. USA, 80:3963–3965). See FIG. 1.

The sequence of the 13,863 bp human CM8 clone was compared with a complete nutleft acid data bank (MicroGenie, Beckman) and showed no homology to any known sequence. However, a 300 bp Alu repeat deficient in the flanking direct repeat sequences was found in the 2.5 kb EcoRI-XhoI fragment (FIG. 3), which explains the Alu type in situ hybridization pattern.

EXAMPLE 6

This example demonstrates the use of the CM8 DNA to form centromeres in mammalian celis.

In order to detect any in vivo centromere iunction of the CM8 DNA, it was introduced with the selectable APH-II gene into mouse LMTK⁻ fibroblast cells. The mouse fibroblast cells were maintained as a monolayer in F12 medium supplemented with 10% FCS. The calcium phosphate method (Harper, et al. (1981), Chromosoma, 83:431–439) was used to transfect the cells with 20 μg λ CM8 and 20 μg λ gtWESneo DNA per Petri dish (80 mm). A 2 minute glycerol shock was used. The λgt WESneo was made by cloning the pAG60 plasmid (Colbere-Garapin, et al. (1981), J. Mol. Biol., 150:1–14) into a λ gtWES (Leder, et al. (1977), Science, 196:175–177) bacteriophage vector.

The whole λ CM8 and λ gt WESneo constructions were used for transfections for two reasons. First, to separate the marker gene from the CM8 sequences, in order to avoid inactivating the APH-II gene, a process which may occur during centromere formation. Second, λ DNA is capable of forming long tandem arrays of DNA molecules by concatamerization. Concatamerization was postulated as being necessary to form centromeres since, in S. pombe 4 to 15 copies of conserved sequence motifs form centromeres (Chikashige, et al. (1989), Cell, 57:739–751). Considering these two facts a multiplication of the putative centromerie DNA by concatamerization might increase the chance of centromere formation.

Transformed celks were selected on growth medium containing 400 μg/ml G418 (Genticin, Sigma). Individual G418 resistant clones were analyzed. The presence of human sequences in the transformed clones was monitored using Southern blots probed with subfragments of the CM8 insert. Screening for excess centromeres was achieved by indirect immunofluorescenee using human anti-centromere serum LU851 (Hadlaezky, et al. (1989), Chromosoma, 97:282–288). The chromosomal localization of "foreign" DNA sequences was determined by in situ hybridization with biotin labelled probes.

Figure 5A:
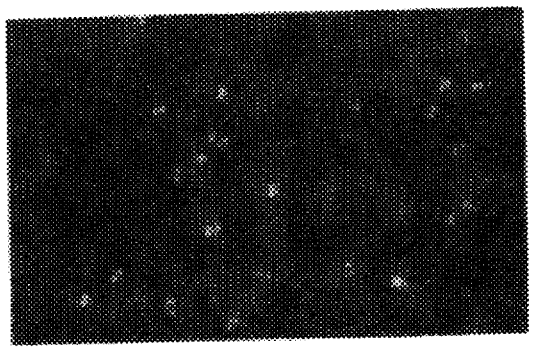

Eight transformed clones have been analyzed. All of the clones contained human DNA sequences integrated into mouse chromosomes. However, only two clones (EC5/6 and EC3/7) showed the regular presence of dicentrie chromosomes. Individual cells of clone EC5/6 carrying di-, tri-, and multicentromerie chromosomes exhibited extreme instability. In more than 60% of the cells of this cell line the chromosomal localization of the integrated DNA sequences varied from cell to cell. Due to this instability, clone EC5/6 was deemed to be unsuitable. However, cells of clone EC3/7 were stable, carrying either a dicentric (85%) or a minichromosome (10%). Centromeres of dicentric chromosomes and minichromosomes were indistinguishable from the normal mouse centromeres by immunostaining with anti-centromere antibodies (FIG. 5A and B).

EXAMPLE 7

This example shows that the newly introduced DNA in the EC3/7 cell line contributes to centromere formation.

In situ hybridization with biotin labelled CM8, APH-II gene, and λ phage DNA were carried out. Chromosomes were counterstained with propidium iodide (Pinkel, et al. (1986), Proc. Natl. Acad. Sci. USA, 83:2934–2938) for in situ hybridization experiments while in indirect immunofluorescence with DNA binding dye, Hoechst 33258 used. All observations and microphotography were made by using an Olympus AHBS Vanox microscope. Forte 400 Professional black and white, and Fujicolor 400 Super HG colour film were used for photographs.

Figure 5E:
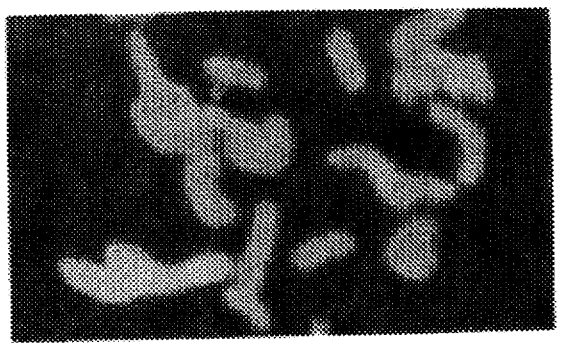
Figure 5B:
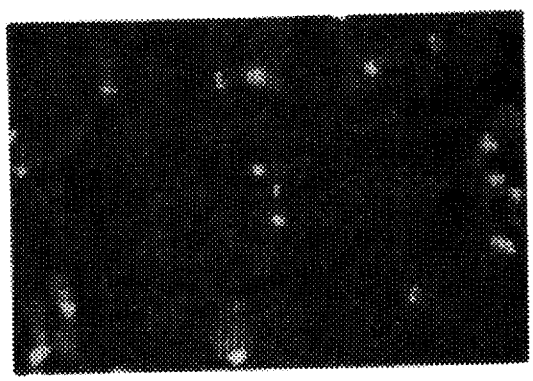
Figure 5F:
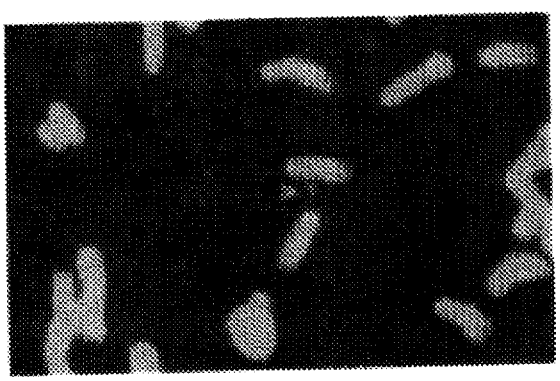
Figure 5C:
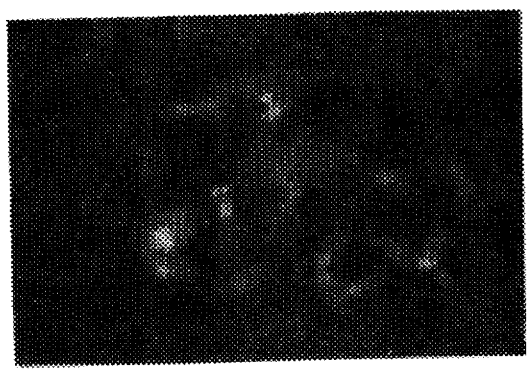
Figure 5G:
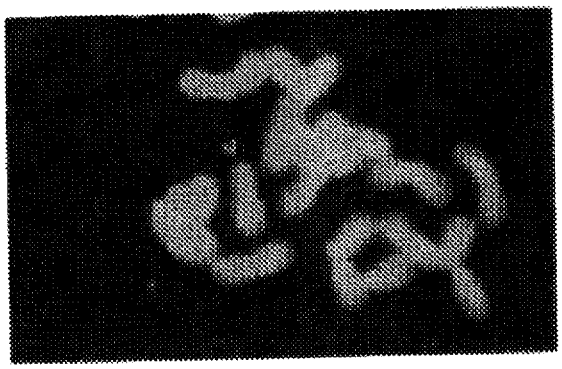
Figure 5D:
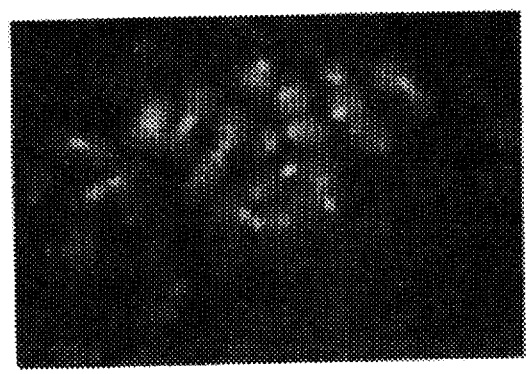

Without exception these three probes hybridized onto the same spots: either on the distal centromere of the dicentric chromosome (FIG. 5C) or on the centromere of the minichromosome (FIG. 5D). In less than 5% of the EC3/7 cells an alternative localization of the hybridization signal was found. These included cells with more than one integration site, cells without a detectable signal, or cells where the hybridization was found on chromosomes other than that identified as the dicentric chromosome.

In less than 0.5% of the cells a tandem array of the hybridization signal was observed on the dicentric chromosomes (FIG. 6A–C), suggesting that the additional centromere was capable of autonomous "duplication." At least some of these duplicated centromeres appeared to be functional. This was indicated by the existence of a minichromosome with double centromeres. Both centromeres of this minichromosome showed positive immunostaining with anti-centromere antibodies (FIG. 7A). Minichromosomes carrying double centromeres might be breakage products of multicentromeric chromosomes.

Indirect immunofluorescence of mouse metaphase cells was performed as described by Hadlaczky, et al. (1989), Chromosoma, 97:282–288. When indirect immunofluorescence and in situ hybridization were performed on the same metaphases, mitotic cells were resuspended in a glycine-hexylene glycol buffer (Hadlaczky, et al. (1989), Chromosoma, 97:282–288), swollen at 37° C. for 10 min followed by cytocentrifugation and fixation with cold (–20° C.) methanol. After the standard immunostaining (Hadlaczky, et al. (1989), Chromosoma, 97:282–288) metaphases were photographed, then coverslips were washed off with phosphate buffered saline and slides were fixed in ice-cold methanol-acetic acid, air-dried and used for in situ hybridization.

To demonstrate the integration of the human CM8 clone sequence and the APH-II gene in the centromere region, immunostaining of centromeres with anti-centromere antibodies followed by in situ hybridization with CM8 and APH-II probes was carried out on the same metaphase plates of EC3/7 cells. The in situ hybridization signals with both biotin-labelled CM8 and APH-II probes showed a colocalization with the immunostained centromeric region of the chromosomes carrying additional centromeres (FIG. 7).

EXAMPLE 8

This example describes the stability of the EC3/7 cell line.

Forty-six independent subclones derived from a single cell were isolated and analyzed. Each of the subclones carried the dicentric chromosome. The percentage of minichromosome-containing cells varied between 2% and 30% in different subclones. We were unable to isolate a subclone which carried the additional centromere exclusively in a minichromosome. This result suggested that the minichromosomes were unstable and they can be regarded as the products of regular breakages of the dicentric chromosomes.

A preliminary analysis by immunostaining of EC3/7 cells (103 metaphases) cultured for 46 days in non-selective medium showed that 80.6% of the cells contained either a dicentric (60.2%) or a minichromosome (20.4%). Subsequent in situ hybridization with biotin labelled probes proved the presence of the "foreign" DNA in the additional centromere. These results indicate that no serious loss or inactivation of the additional centromeres had occurred during this period of culture under non-selective conditions.

EXAMPLE 9

This example shows that the CM8 insert concatamerized to form the functioning centromere of cell line EC3/7.

DNA of the EC3/7 cell line and human lymphocyte DNA were digested with restriction endonucleases and probed with subfragments of the CM8 insert in a Southern hybridization experiment. Comparing the intensity of the hybridization signal with EC3/7 DNA to that with the human DNA, the minimum number of integrated human sequences in the additional centromere was estimated to be ≧30. The copy number of CM8 in human lymphocytic DNA was determined as described above in Example 3.

I claim:

1. A method of producing a mammalian cell containing an excess of functional centromeres, comprising:
   (a) cotransfecting cells with a DNA fragment comprising human DNA and a DNA fragment encoding a dominant selectable marker, wherein the cotransfected human DNA fragment comprises CM8,
   (b) growing the cells and selecting cells that express the dominant selectable marker;
   (c) detecting among the cells that express the dominant selectable marker those cells with an excess of mammalian centromeres.

2. The method of claim 1, wherein the human DNA fragment comprises the sequence of nucleotides set forth in FIG. 1.

3. The method of claim 1, wherein the cells that express the dominant selectable marker and have an excess of mammalian centromeres are cells that have all of the identifying characteristics of the cells deposited at the European Collection of Animal Cell Cultures (ECACC) under accession no. 90051001.

4. The method of claim 1, wherein the human DNA is contained in the clone λCM8 and the selectable marker is encoded by λgtWESneo.

5. A method of producing mammalian cells containing a dicentric chromosome, comprising:
   (a) cotransfecting cells with a DNA fraqment comprising human DNA and a DNA fraqment encoding a dominant selectable marker, wherein the human DNA fragment comprises the human DNA in the clone λCM8;
   (b) growing the cells under selective conditions and selecting cells that express the dominant selectable marker;
   (c) detecting among the cells that express the dominant selectable marker those cells with an excess of mammalian centromeres that include a chromosome with two centromeres.

6. The method of claim 5, wherein the transfected DNA comprising human DNA comprises the sequence of nucleotides set forth in FIG. 1.

7. A method of producing mammalian cells containing a minichromosome that contains heterologous DNA, comprising:
   (a) cotransfecting cells with a DNA and a DNA fragment comprising human DNA and a DNA fragment encoding a dominant selectable marker, wherein the human DNA fragment comprises the human DNA in the clone λCM8;
   (b) growing the cells under selective conditions and selecting cells that express the dominant selectable marker;
   (c) detecting among the cells that express the dominant selectable marker those cells with an excess of mammalian centromeres that include a minichromosome, wherein the minichromosome is smallest chromosome in the cell.

8. The method of claim 7, wherein the transfected DNA comprising human DNA comprises the sequence of nucleotides set forth in FIG. 1.

9. A method of producing a mammalian cell containing an excess of centromeres, comprising:
   (a) cotransfecting cells with a DNA fragment comprising the sequence of nucleotides set forth in FIG. 1 and a DNA fragment encoding a dominant selectable marker;
   (b) growing the cells and selecting cells that express the dominant selectable marker;
   (c) detecting among the cells that express the dominant selectable marker those cells with an excess of mammalian centromeres.

10. The method of claim 9, wherein the selectable marker encodes aminoglycoside-3' phosphotransferase-II.

11. A method of producing a mammalian cell containing an excess of functional centromeres, comprising:
   cotransfecting cells with a DNA fragment comprising human DNA and a DNA fragment encoding a dominant selectable marker, wherein the human DNA comprises the sequence of nucleotides set forth in FIG. 1.

* * * * *

UNITED STATES PATENT AND TRADEMARK OFFICE
CERTIFICATE OF CORRECTION

PATENT NO.: 5,712,134

DATED: January 27, 1998

INVENTOR(S): Hadlaczky, G.

Figure 4A:
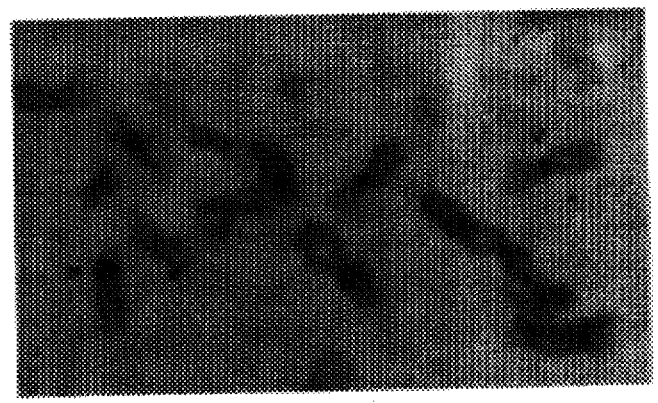
Figure 4B:
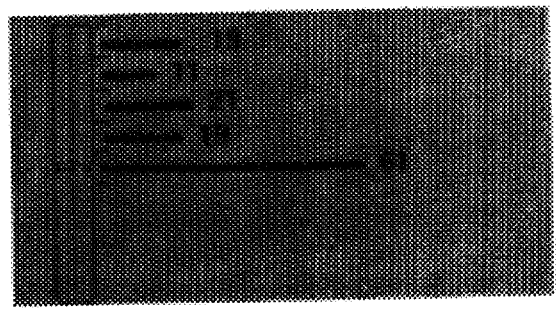
Figure 5H:
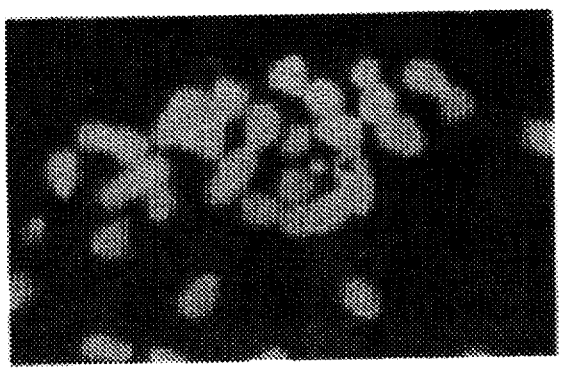
Figure 6A:
Figure 6B:
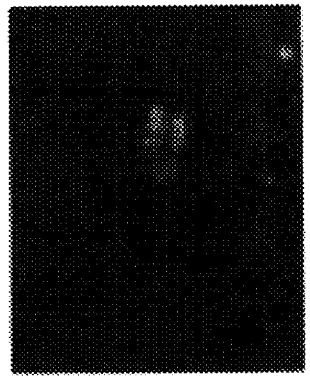
Figure 6C:
Figure 6D:
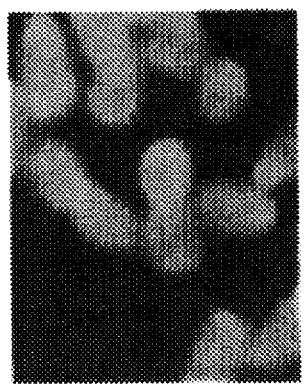
Figure 6E:
Figure 6F:
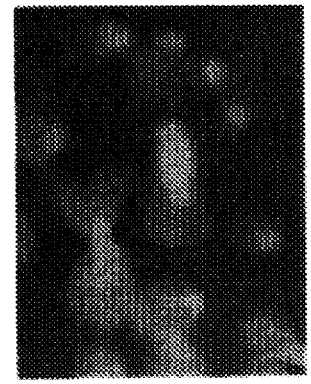
Figure 7A:
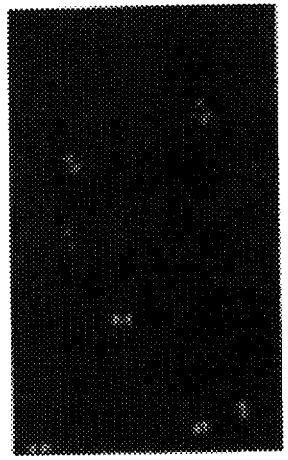
Figure 7B:
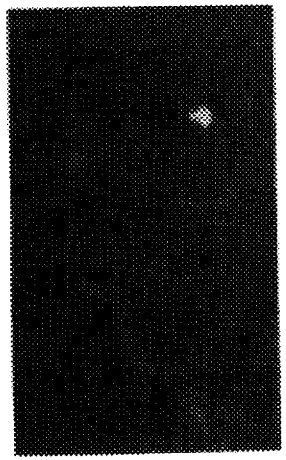
Figure 7C:
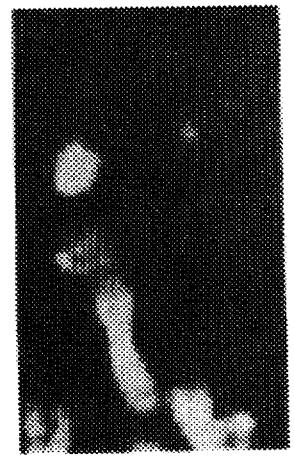
Figure 7D:
Figure 7E:
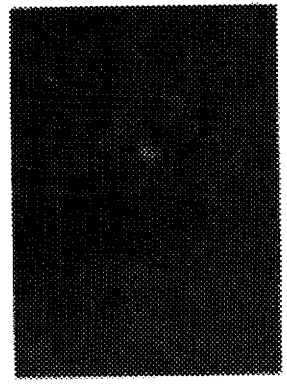
Figure 7F:
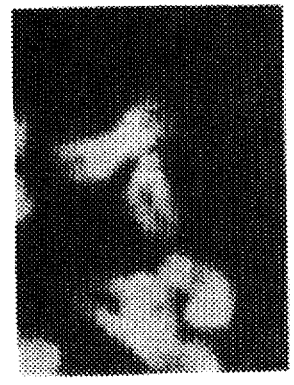

It is certified that error appears in the above-identified patent and that said Letters Patent is hereby corrected as shown below:

at column 2, line 3, replace "Figure 1" with —Figures 1A-1L—
at column 2, line 36, replace "Figure 1" with —Figures 1A-1L—
at column 2, line 53, replace "Figure 4 shows" with —Figures 4A and 4B show—
at column 2, line 56, replace "Panel A" with —Figure 4A—
at column 2, line 58, replace "Panel B" with —Figure 4B—
at column 2, line 62, replace "Figure 5 shows" with —Figures 5A-5H show—
at column 2, line 64, replace "panels A and B" with —Figures 5A and 5B—
at column 2, line 65, replace "panel C" with —Figure 5C—
at column 2, line 67, replace "panel D" with —Figure 5D—
at column 3, line 1, replace "Panels E and F" with —Figures 5E and 5F—
at column 3, line 2, replace "Panels G and H" with —Figures 5G and 5H—
at column 3, line 2, replace "Panels" with —Figures—
at column 3, line 3, replace "E-H correspond to A-D" with —5E-5H correspond to Figures 5A-5D—
at column 3, line 5, replace "Figure 6 shows" with —Figures 6A-6F show—
at column 3, line 7, replace "Panels A-C" with —Figures 6A-6C—
at column 3, line 9, replace "Panels D-F" with —Figures 6D-6F—
at column 3, line 9, replace "A-C" with —Figures 6A-6C—
at column 3, line 11, replace "Figure 7 demonstrates" with —Figures 7A-7F illustrate—
at column 3, lines 13 and 14, replace "Panels A and D" with —Figures 7A and 7D—
at column 3, line 14, replace "panel B" with —Figure 7B—
at column 3, line 14, replace "panel E" with —Figure 7E—
at column 3, line 17, replace "Panels C and F" with —Figures 7C and 7F— at column 4, line 55, replace "Figure 1" with —Figures 1A-1L—
at column 4, line 60, replace "Figure 1" with —Figures 1A-1L—
at column 6, line 31, replace "Fig. 4" with —Figures 4A and 4B—
at column 6, line 56, replace "Figure 1" with —Figures 1A-1L—
at column 7, line 51, replace "Fig. 5A and B" with —Figures 5A and 5B—
at column 8, line 10, replace "Fig. 6A-C" with —Figures 6A-6C—
at column 8, line 41, replace "Fig. 7" with —Figures 7A-7F—

UNITED STATES PATENT AND TRADEMARK OFFICE
CERTIFICATE OF CORRECTION

PATENT NO.: 5,712,134

DATED: January 27, 1998

INVENTOR(S): Hadlaczky, G.

It is certified that error appears in the above-identified patent and that said Letters Patent is hereby corrected as shown below:

IN THE CLAIMS:

Delete claims 2, 7, 9, 10 and 11 and replace with the following claims:

—2. The method of claim 41, wherein the human DNA fragment comprises the sequence of nucleotides set forth in Figures 1A-1L.—

—7. A method of producing a mammalian cell containing an excess of centromeres, comprising:

(a) cotransfecting cells with a DNA fragment comprising the sequence of nucleotides set forth in Figures 1A-1L and a DNA fragment encoding a dominant selectable marker;
(b) growing the cells and selecting cells that express the dominant selectable marker;
(c) detecting among the cells that express the dominant selectable marker those cells with an excess of mammalian centromeres.—

—9. A method of producing a mammalian cell containing an excess of functional centromeres, comprising:

cotransfecting cells with a DNA fragment comprising human DNA and a DNA fragment encoding a dominant selectable marker, wherein the human DNA comprises the sequence of nucleotides set forth in Figures 1A-1L.—

—10. The method of claim 46, wherein the transfected DNA comprising human DNA comprises the sequence of nucleotides set forth in Figures 1A-1L.— and —11. The method of claim 48, wherein the transfected DNA comprising human DNA comprises the sequence of nucleotides set forth in Figures 1A-1L.—

Signed and Sealed this

Twenty-second Day of June, 1999

Attest:

Q. TODD DICKINSON

*Attesting Officer*   *Acting Commissioner of Patents and Trademarks*